US011173128B2

(12) United States Patent
Sunderland

(10) Patent No.: US 11,173,128 B2
(45) Date of Patent: Nov. 16, 2021

(54) NANOSPUN HEMP-BASED MATERIALS

(71) Applicant: Thomas Jefferson University, Philadelphia, PA (US)

(72) Inventor: Mark Sunderland, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 16/395,797

(22) Filed: Apr. 26, 2019

(65) Prior Publication Data

US 2019/0328678 A1 Oct. 31, 2019

Related U.S. Application Data

(60) Provisional application No. 62/663,716, filed on Apr. 27, 2018.

(51) Int. Cl.
*A61K 9/70* (2006.01)
*A61K 31/05* (2006.01)

(52) U.S. Cl.
CPC ............... *A61K 9/70* (2013.01); *A61K 31/05* (2013.01)

(58) Field of Classification Search
CPC .................................. A61K 31/05; A61K 9/70
See application file for complete search history.

(56) References Cited

U.S. PATENT DOCUMENTS

| 9,340,475 | B2 | 5/2016 | Mona, III et al. | |
|---|---|---|---|---|
| 2016/0002133 | A1* | 1/2016 | Mona, III | C11B 3/00 568/807 |
| 2016/0374958 | A1* | 12/2016 | Anastassov | A61K 31/05 514/734 |
| 2017/0231231 | A1 | 8/2017 | Enan | |

FOREIGN PATENT DOCUMENTS

| WO | WO/2009/045042 A1 | 4/2009 | |
|---|---|---|---|
| WO | WO-2009045042 A1 * | 4/2009 | ............. D01D 5/003 |

OTHER PUBLICATIONS

Novak et al., "Essential oils of different cultivars of *Cannabis sativa* L. and their antimicrobial activity", 2001, Flavour and Fragrance Journal, vol. 16, pp. 259-262. (Year: 2001).*
Dasdemir et al., "Electrospinning of Thermoplastic Polyurethane Microfibers and Nanofibers from Polymer Solution and Melt", 2013, Journal of Applied Polymer Science, vol. 127, pp. 1901-1908. (Year: 2013).*
Teh et al., "Physicochemical and quality characteristics of cold-pressed hemp, flax and canola seed oils", 2013, Journal of Food Composition and Analysis, vol. 30, pp. 26-31. (Year: 2013).*
Lin et al., "Antibacterial properties of nanofibers containing chrysanthemum essential oil and their application as beef packaging", 2019, available online Dec. 8, 2018, International Journal of Food Microbiology, vol. 292, pp. 21-30. (Year: 2018).*
Prabuseenivasan et al., "In vitro antibacterial activity of some plant essential oils", BMC Complementary and Alternative Medicine, Nov. 30, 2006, vol. 6, No. 1, pp. 1-8. (Year: 2006).*
"Specialty Crops Factsheet: Industrial Hemp", British Columbia Ministry of Argiculture and Food, Sep. 1999.
Ali, et al., "Antimicrobial Activity of *Cannabis Sativa* L.", Chinese Medicine, vol. 3, No. 1, Mar. 2012, 61-64.
Averink, Global Water Footprint of Industrial Hemp Textile, Sep. 2015.
Banks, et al., A New Textiles Economy: Redesigning Fashion's Future, Nov. 28, 2017.
Baxter, et al., "Growing Industrial Hemp in Ontario", Aug. 2000, www.omafra.gov.on.ca/english/crops/facts/00-067.htm.
Brook, et al., Industrial Hemp Harvest and Storage: Best Management Practices, Nov. 10, 2015.
CAB International, "*Cannabis sativa* (Hemp) Datasheet", Invasive Species Compendium, Nov. 6, 2018, www.cabi.org/isc/datasheet/14497.
Canadian Hemp Trade Alliance, Hemp Production eGuide, 2018, www.hemptrade.ca/eguide.
Carpenter, "In Kentucky, Farmers Find Hemp May Be More Profitable Than Tobacco", Forbes, Aug. 28, 2018, www.forbes.com/sites/workday/2019/06/18/5-steps-financial-leaders-can-take-to-cultivate-innovation/#21e703bf5a30.
Cherrett, et al., Ecological Footprint and Water Analysis of Cotton, Hemp and Polyester, 2005.
Collier, et al., Textile Testing and Analysis, 1999.
Danish Fashion Institute, "Material Snapshot: Hemp", Jun. 7, 2018, designforlongevity.com/articles/material-snapshot-hemp.
Dvorak, "History of Hemp in America", CBD Oiled, 2004, cbdoiled.com/history-of-hemp-in-america/.
Fabriclink, "Fiber Characteristics: Hemp", www.fabriclink.com/University/Hemp.cfm.
Górski, et al., "The Effect of Hemp Essential Oil on Mortality Aulacorthum Solani Kalt. and Tetranychus Urticae Koch", Ecological Chemistry and Engineering S, vol. 23, No. 3, Oct. 20, 2016, 505-511.
Günther, "Carbon Sequestration for Everybody: Decrease Atmospheric Carbon Dioxide, Earn Money and Improve the Soil", Energy and Environment, Mar. 27, 2007.
James, "Top 6 Hemp Growing Countries: USA Now Ranks No. 3!", Ministry of Hemp, Apr. 22, 2019, ministryofhemp.com/blog/hemp-growing-countries/.
Johnson, "Hemp as an Agricultural Commodity", Congressional Research Service, Jun. 22, 2018.
Johnston, "The Environmental Benefits of Industrial Hemp", Virginia Industrial Hemp Coalition, Feb. 2016.
Liakos, et al., "Electrospun Fiber Pads of Cellulose Acetate and Essential Oils with Antimicrobial Activity", Nanomaterials, vol. 7, No. 4, Apr. 12, 2017, 1-10.

(Continued)

*Primary Examiner* — Michael B. Pallay
(74) *Attorney, Agent, or Firm* — Vos-IP, LLC

(57) ABSTRACT

An antibacterial composite material comprising at least 10% of a hemp oil, said hemp oil comprising CBD at a concentration of at least 10 mg/ml and a polymer formed by a process wherein said hemp oil and said polymer are dissolved into a solvent and said solvent is expressed through a spinneret, wherein a voltage is applied at up to 100 kV, wherein the solvent is pressed through the spinneret and forming the antibacterial composite material on a collector.

8 Claims, 13 Drawing Sheets

(56) References Cited

OTHER PUBLICATIONS

Manitoba Agriculture, "Industrial Hemp Production and Management", www.gov.mb.ca/agriculture/crops/production/hemp-production.html.

Manning, et al., "US President Donald Trump Signs 2018 Farm Bill Into Law", Produce Grower, Dec. 21, 2018, www.producegrower.com/article/us-president-donald-trump-sign-2018-farm-bill-law/.

Montford, et al., "A Comparison of the Biodiversity Friendliness of Crops With Special Reference to Hemp (*Cannabis sativa* L.)", Journal of the International Hemp Association, vol. 6 No. 2, Dec. 1999, 53-63.

Newland, "Hemp Politics—Why Was Hemp Made Illegal In 1937?", CBD Oiled, cbdoiled.com/why-was-hemp-made-illegal-in-1937/.

O'Connell, "How Hemp Can Heal Our Soil & Why It Matters To Consumers", Ministry of Hemp, Apr. 27, 2017.

Palmer, "High on Environmentalism", Slate, Apr. 12, 2011, slate.com/technology/2011/04/hemp-versus-cotton-which-is-better-for-the-environment.html.

Roth, et al., "Industrial Hemp Production", Penn State Extension: Agricultural Alternatives, Jul. 2, 2018.

Salentijn, et al., "New Developments in Fiber Hemp (*Cannabis sativa* L.) Breeding", Industrial Crops and Products, vol. 68, Sep. 2, 2014, 32-41.

Schiller, "President Trump Signs 2018 Farm Bill, Legalizing Hemp", Cannabis Business Times, Dec. 20, 2018, www.cannabisbusinesstimes.com/article/president-trump-signs-2018-farm-bill-legalizing-hemp/.

Small, et al., "Hemp: A New Crop with New Uses for North America", Trends in New Crops and New Uses, 2002, 284-326.

Van Der Werf, et al., "The Environmental Impacts of the Production of Hemp and Flax Textile Yarn", Industrial Crops and Products, vol. 27, No. 1, Jan. 2008, 1-10.

Wicker, "Could Hemp Fashion Be the Key to Fixing India's Cotton Economy?", Forbes, Oct. 23, 2017, www.forbes.com/sites/ashoka/2017/10/23/could-hemp-fashion-be-the-key-to-fixing-indias-cotton-economy/#6518ae43106a.

* cited by examiner

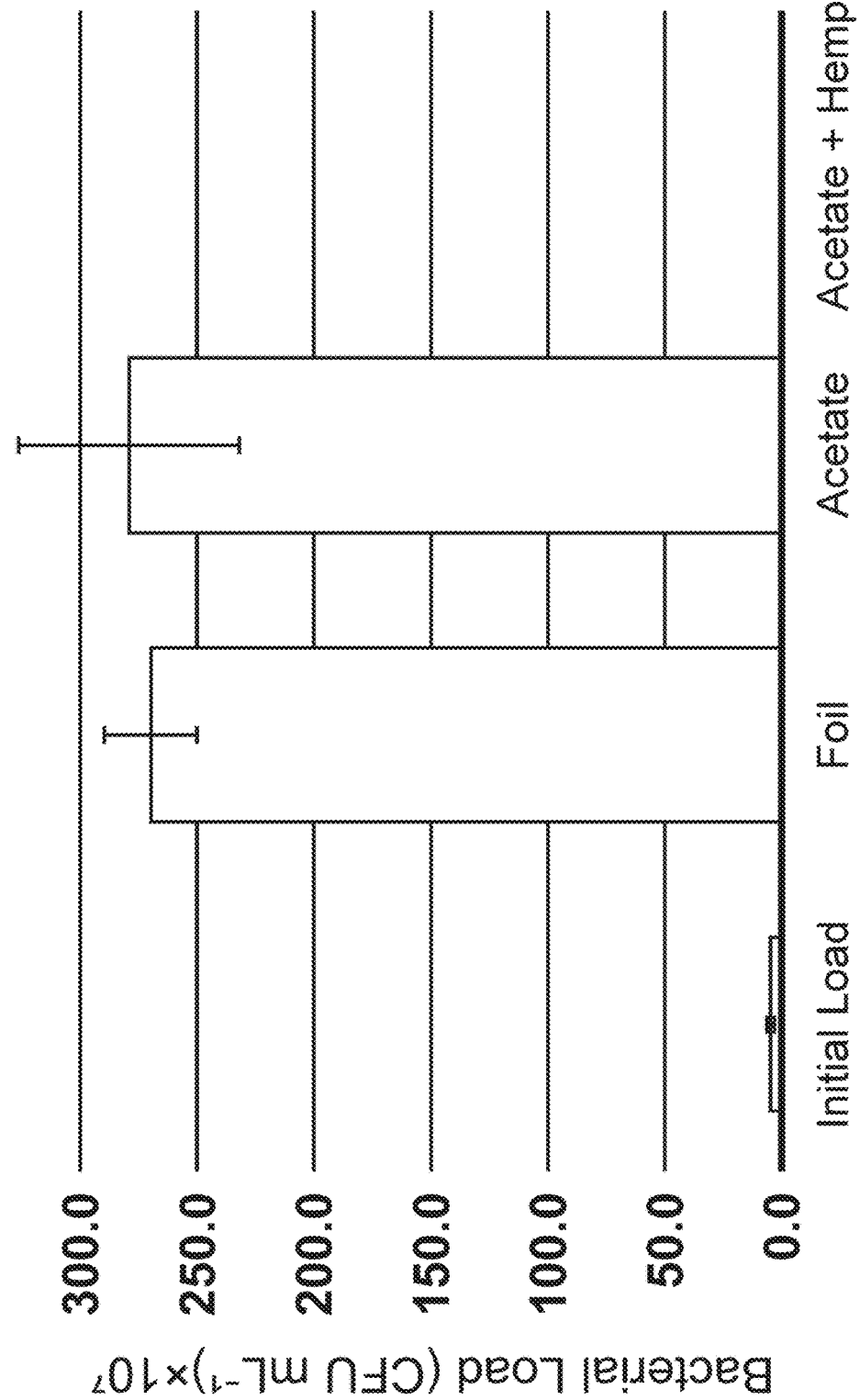

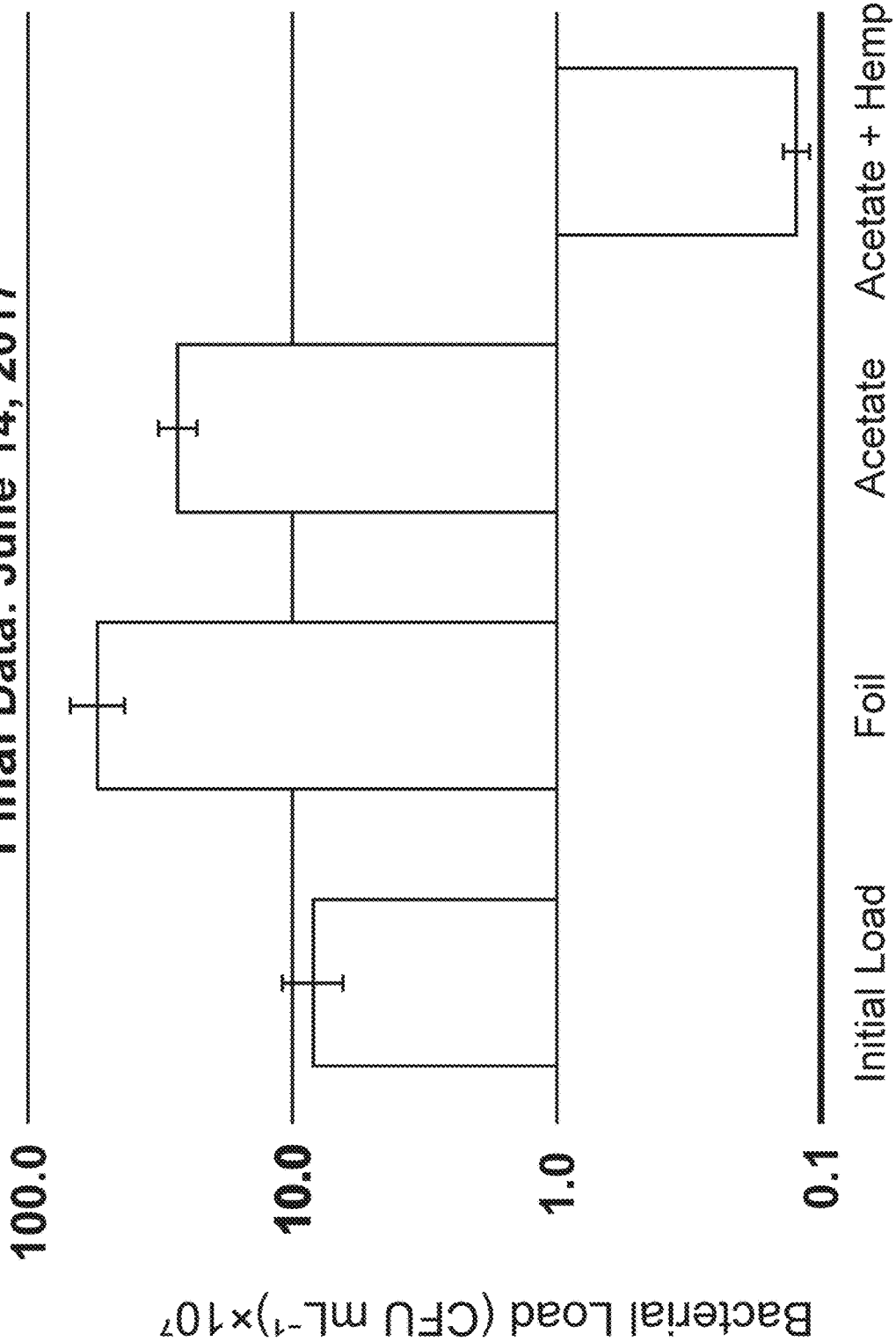

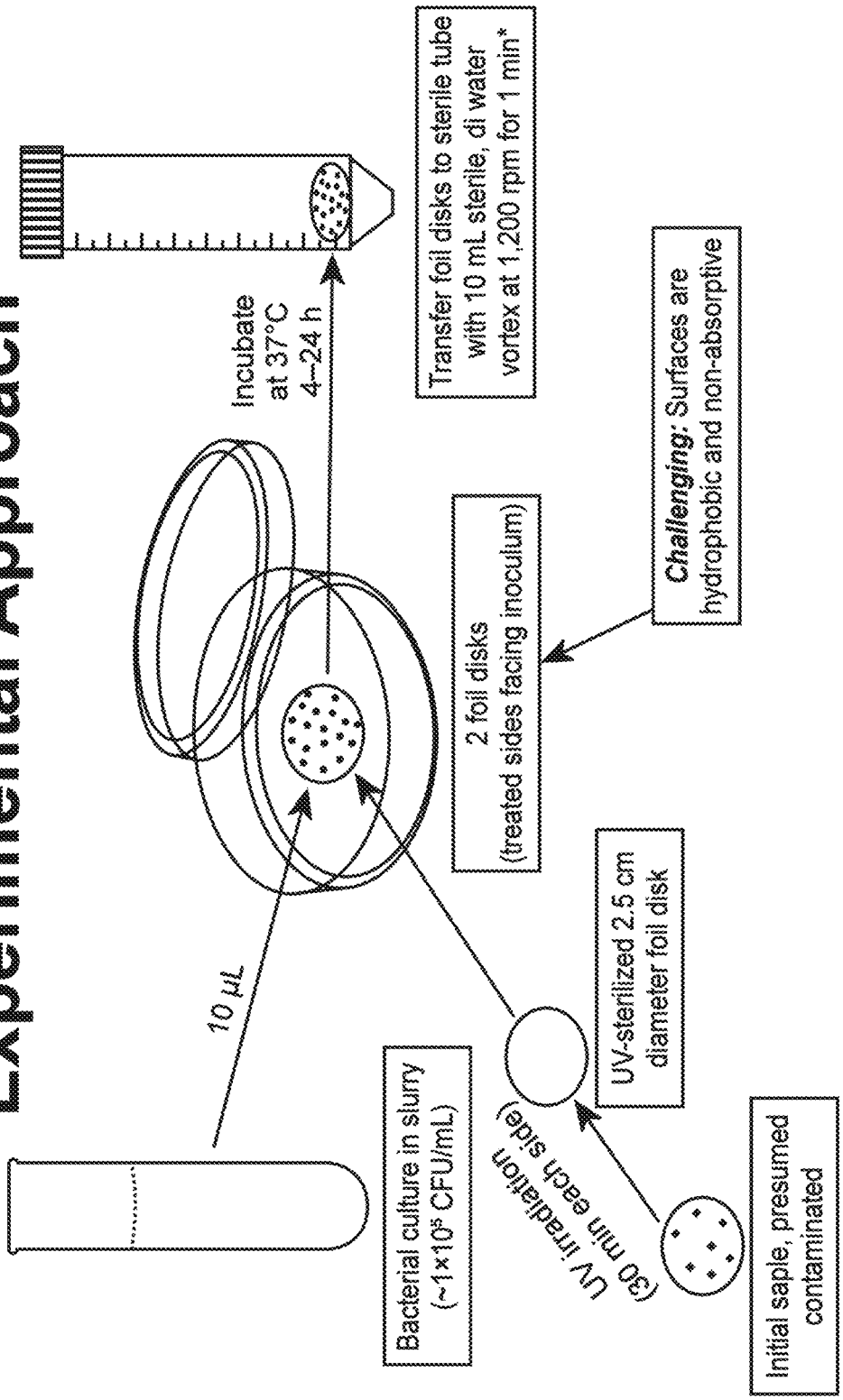

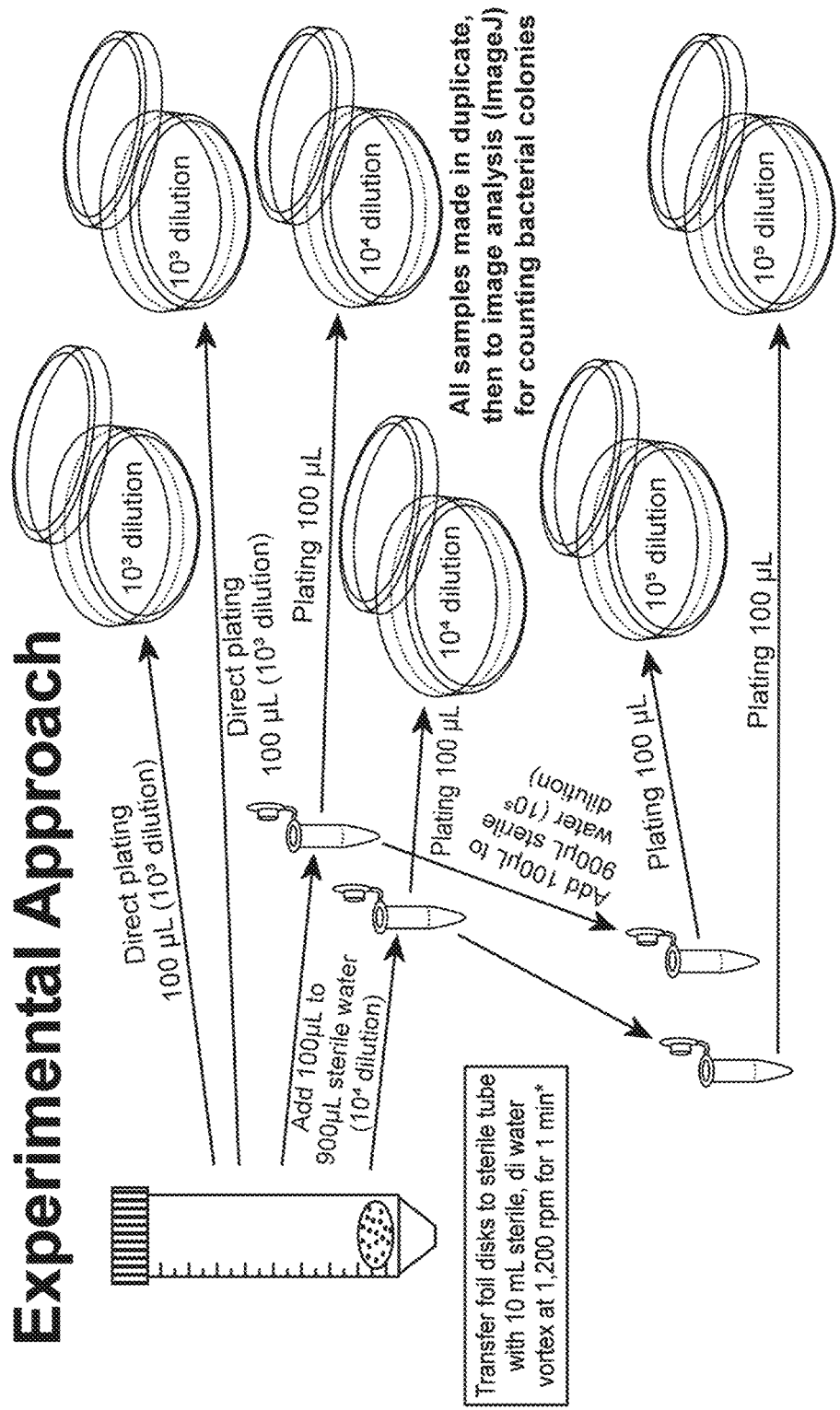

FIGURE 9

Experimental Timeline: 4h Incubation

| Day 1 | Day 2 | Day 3 | Ongoing |
|---|---|---|---|
|  | <u>9–11 AM:</u><br>• Standardize overnight culture<br>• Prepare inoculation slurry<br>• UV sterilize foil pieces | <u>9 AM:</u><br>• Take pictures of plates | • Preparation of media (plates, broth, slurry)<br><br>• Maintenance of cultures<br><br>• Maintenance of waste<br><br>• Sterilization of supplies (tips, foreceps, etc.)<br><br>• Image analysis |
|  | <u>11 AM:</u><br>• Apply bacteria to foil |  |  |
|  | <u>11:05 AM:</u><br>• Dilute and plate inoculum (6 plates total) |  |  |
| <u>3–4 PM:</u><br>• Start overnight culture | <u>1 PM:</u><br>• Dilute and plate samples (16–24 plates total) |  |  |

NANOSPUN HEMP-BASED MATERIALS

PRIORITY CLAIM

This application claims the benefit of U.S. Provisional Application No. 62/663,716 filed Apr. 27, 2018, which is incorporated by reference herein in its entirety.

FIELD OF INVENTION

The present application is generally related to nano spun materials comprising of oil and polymers, which have certain antibacterial and other properties, wherein the materials can be utilized to generate technical properties in fabric materials.

BACKGROUND

Hemp is one of several plant species typically found in the northern hemisphere, of the variety of the Cannabis sativa plant species. It is one of the fastest growing terrestrial plants and was one of the first plants to be spun into fibers, some 10,000 years ago. A hemp crop has the potential of yielding 3-8 tons of dry stalks per acre per season. Hemp is naturally resilient to weeds and can be harvested 2-3 times year. Hemp does not need pesticides or herbicides and requires less water and fertilizer to flourish other ops like cotton farmed for textile applications. Hemp can be further utilized to clear fields, rest fields, and functions as a carbon negative plant.

The average hemp plant grows to a height of between six (6) feet to sixteen (16) feet and matures in approximately seventy (70) to one hundred ten (110) days. A hemp crop has the potential of yielding 3-8 tons of dry stalks per acre. Hemp has many advantages over other agricultural crops, namely, the plant itself is resilient to weeds, it can be harvested 2-3 times a season and it does not need pesticides or herbicides to flourish. Its deep root system means that hemp plants need less nitrogen (fertilizer) and water to flourish. Moreover, farmers can use hemp plants as an alternative to clear fields for other crops.

Hemp, like many dicotyledonous plants contains a phloem and fibers around the phloem. Hemp is no different and contains both a fiber (bast fiber) as well as a hurd portion. The fibers may be separated from the hurd by mechanical (for example, decortication), or chemical properties, and the fibers can then be used for any fiber materials, including textiles like carpet, yarn, rope, netting, matting, and the like. The hurd, by contrast, is relatively difficult to use, and has been used only for processes such as paper-making, particleboards, concrete mixtures and construction composites, as well as for animal bedding.

The properties of the hemp plant allow it to be refined into a number of commercial items including paper, textiles, clothing, biodegradable plastics, paint additive, insulative materials, biofuels, as well as a food source through use of the hurd and fiber portions of the stalk. However, certain varietals of hemp are also known for their concentrations of certain cannabinoid compounds, terpene compounds, and other compounds that may be isolated for further use.

Of the most widely known compounds from the help plant is tetrahydrocannabinol (THC). Unfortunately, the psychoactive properties of THC have led to limitations on hemp cultivation, despite many varietals having low to no concentrations of this compound. Other varietals, however, are known for flowers and seeds which are used to produce cannabidiol oil (CBD) oil. Many strains of hemp have been selectively bred to increase the concentrations of phytochemical compositions such as THC, while others are higher in those such as CBD. Yet, because of the implications in the United States for cultivation of the THC containing materials, hemp is highly restricted.

The hemp seeds themselves can be eaten raw, ground into a meal, or made into a dried powder. Leaves can also be consumed raw or cooked for consumption. These materials can also be made into a liquid for baking or for beverages including hemp milk, hemp juice, and teas. In particular, hemp oil is often cold-pressed from seeds and is high in unsaturated fatty acids. 100 grams of hulled hemp seeds supply 586 calories, with approximately 5% water, 5% carbohydrates, 49% total fat, and 31% protein. Hemp seeds are also a rich source of B vitamins, manganese, phosphorous, magnesium, zinc, iron, and dietary fiber. Hemp oil, unfortunately, oxidizes at a rapid rate and turns rancid in a short period of time and thus must be properly controlled and formulated for stability. For example, controlled conditions, namely darkness and reduction of oxygen, and cold temperatures can increase the shelf-life, though it remains a short period as compared to other known oils, including olive and other vegetable oils. These oils are used, typically in full strength, or diluted with a carrier and topically applied.

Hemp oil derived from hemp seeds, contains antibacterial, antiviral, antifungal, antioxidant, anti-inflammatory and cardioprotective properties. Furthermore, the oil can be used topically as a skin regenerative. Additional oils, including those in the botanical oil and essential oil families are known to have other properties, some which, like hemp oil, have useful properties for antibacterial, antiviral, antifungal, antioxidant, anti-inflammatory, and cardio-protection. While others are useful for their botanical notes, and other suitable uses.

CBD oil may also be produced from hemp plants; however, it is extracted from leaves, flowers, and stems of the hemp plant. CBD oil, like hemp oil, has certain anti-inflammatory properties.

Herein embodiments describe a process and method for combining oils with certain polymer materials, enabling an infused polymer to capture properties of the oil, and Applicant has further generated new materials and compositions of matter that comprise at least one oil and a polymer carrier, that surprisingly imparts properties of the oil into textiles made form a combination of the oil and polymer.

SUMMARY OF THE INVENTION

A preferred embodiment is directed towards a method of manufacturing a new composite material comprising hemp-based oils, dissolving the hemp-based oil and a polymer into a solution of acetone, and extruding the solution of acetone to form a nanospun filament. In a further preferred embodiment, the hemp-based oil is an extracted oil high in CBD (greater than 10% CBD), and the polymer is acetate.

In a preferred embodiment, a method of manufacturing a fiber comprising between 1 and 30% of at least one oil and between 99% and 70% of at least one polymer; wherein the oil and polymer are combined and extruded via electrospinning to form a fiber or film comprising the combined oil and polymer.

In a preferred embodiment, an electro spun film or fiber comprising between 1 and 30% of at least one oil and between 99% and 70% of at least one polymer. In preferred embodiments, the at least one oil is derived from cannabis plants, and preferable is CBD oil. In a further preferred embodiment, the at least one oil comprises at least two oils, a first oil of CBD oil and a second oil selected from the group consisting of: allspice, angelica, anise, basil, bay leaf, benzoin, bergamot, birch, bitter almond, black pepper, boldo, buchu, cajuput, calamus, chamomile, camphor, caraway, cardamom, carrot seed, cassia, catnip, cedarwood, chrysanthemum, cinnamon, citronella, clary sage, clove, coriander, cumin, cypress, davana, dill, elemi, eucalyptus, fennel, frankincense, galbanum, geranium, ginger, grapefruit, helichrysum, hemp, hyssop, jasmine, juniper, lavandin, lavender, lemon, lemongrass, lime, mandarin, manuka, marjoram, melissa, mugwort, mullein, mustard, myrrh, myrtle, neroli, niaouli, nutmeg, oakmoss, orange, oregano, palma rosa, parsley, patchouli, pennyroyal, peppermint, petitgrain, pimento, pine, ravensara, rose, rosemary, rosewood, rue, sage, sandalwood, spearmint, spikenard, tagetes, tangerine, tansy, tarragon, tea tree, thuja, thyme, tuberose, vanilla, vetiver, wintergreen, wormwood, yarrow, ylang, and combinations thereof.

In a preferred embodiment, a method of manufacturing a nano composite material wherein the composite material comprises between 5 and 30% CBD oil and 70% to 95% of a polymer, with each percentage being a percent weight of the total composition. In a preferred embodiment, the polymer is acetate. In a preferred embodiment, the CBD oil and acetate are dissolved in an acetone solution. In a preferred embodiment, the acetone solution is between 50 and 99% acetone.

In a preferred embodiment, a method of manufacturing a composite material comprising of extracting a portion of oil from a hemp flower, leaves, stalk, and combinations thereof; dissolving the extracted oil into a nonaqueous solvent; dissolving a second material into said nonaqueous solvent; extruding the material having both the extracted oil and second material into a nanospun fiber. Preferably the extracted oil comprises at least 5% cannabidiol ("CBD"), and more preferably at least 10% CBD, and most preferably, at least 15% CBD, or 20% CBD. In a further preferred embodiment, the oil is a cold-pressed hemp seed oil, which is further enriched with certain terpenes including B-myrcene, B-Caryophyllene, Linalool, a-Pinene, Citral, d-Limonene, and Eucalyptol. Such terpenes can be naturally or synthetically derived and added at between 0-10% of the total weight of the hemp seed oil. In a preferred embodiment, the hemp oil is enriched with a 1% solution of terpenes comprising:

| | |
|---|---|
| B-Myrcene | 20% |
| B-Caryophyllene | 20% |
| Linalool | 8% |
| a-Pinene | 8% |
| Citral | 25% |
| d-Limonene | 17% |
| Eucalyptol | 2% |

In a preferred embodiment, the nonaqueous solvent is acetone.

In a preferred embodiment, the portion of oil comprises between 0.1 and 50% of the total weight of the composite material. In a preferred embodiment, wherein the portion of oil comprises between 5 and 25% of the total weight of the composite material. In a preferred embodiment, wherein the portion of oil comprises between 5 and 15% of the total weight of the composite material.

In a preferred embodiment, a nanospun fiber further comprises a third component which is effective in reducing the population of gram-negative bacteria when such gram-negative bacteria contacts said third component.

In a preferred embodiment, a nanospun fiber comprising between 0.1 and 25% CBD oil and 99.9 and 75% acetate.

In a further preferred embodiment, a nanospun fiber comprising between 1-20% CBD oil, 1-20% of a second oil, and 60-98% of a polymer.

In a preferred embodiment, a nanospun fiber comprising a CBD oil and a polymer, wherein said fiber is manufactured by dissolving said CBD oil and said polymer into acetate, wherein said polymer is acetate, and extruding said acetone comprising the CBD oil and acetate into a nanospun fiber. In a preferred embodiment, the nanospun fiber further comprising a material effective in treating gram-negative bacteria.

In a further preferred embodiment, a method of manufacturing a nanospun fiber comprising hemp oil and acetate; dissolving the hemp oil and acetate into a solution of acetone and extruding the solution of acetone to form the nanospun fiber.

In a further embodiment, the method wherein the hemp oil is a cannabidiol ("CBD") oil, comprising at least 10 mg/ml CBD.

In a further embodiment, the method wherein the composite material comprises 10% hemp oil and 90% acetate, with each percentage being a percent weight of the total composition.

In a further embodiment, the method wherein the acetone solution is between 50 and 99% acetone.

In a further embodiment, the method wherein the hemp oil comprises a CBD extract having a concentration of CBD of at least 10 mg/ml.

In a further preferred embodiment, a method of manufacturing a composite material comprising of extracting a portion of oil from a hemp plant to form an extracted hemp oil; dissolving the extracted hemp oil into a nonaqueous solvent; dissolving a second material into said nonaqueous solvent; extruding the material having both the extracted hemp oil and second material into a nanospun fiber.

In a further embodiment, the method wherein the extracted hemp oil comprises at least 10 mg/ml CBD, and a carrier oil.

In a further embodiment, the method wherein the nonaqueous solvent is acetone.

In a further embodiment, the method wherein the portion of extracted hemp oil comprises between 0.1 and 50% of the total weight of the composite material.

In a further embodiment, the method wherein the portion of extracted hemp oil comprises between 5 and 25% of the total weight of the composite material.

In a further embodiment, the method wherein the portion of extracted hemp oil comprises between 5 and 15% of the total weight of the composite material.

In a further embodiment, the method further comprising a third component which is effective in reducing the population of gram-negative bacteria when such gram-negative bacteria contact said third component.

In a further embodiment, the method wherein the extracted hemp oil comprises at least 20 mg/ml CBD. In a further embodiment, the method wherein the extracted hemp oil comprises at least 40 mg/ml CBD. In a further embodiment, the method wherein the extracted hemp oil comprises at least 50 mg/ml CBD.

In a further preferred embodiment, a nanospun fiber comprising between 0.1 and 25% hemp oil and 99.9 and 75% acetate.

In a further embodiment, the nanospun fiber wherein said fiber is manufactured by dissolving said hemp oil and said acetate into acetone to form an acetone solution and extruding said acetone solution into a nanospun fiber.

In a further embodiment, the nanospun fiber comprising a material effective in treating gram-negative bacteria.

In a further embodiment, the nanospun fiber comprising about 10% hemp oil and about 90% acetate.

In a further embodiment, the nanospun fiber further comprising at least one further oil selected from the group consisting of: allspice, angelica, anise, basil, bay leaf, benzoin, bergamot, birch, bitter almond, black pepper, boldo, buchu, cajuput, calamus, chamomile, camphor, caraway, cardamom, carrot seed, cassia, catnip, cedarwood, chrysanthemum, cinnamon, citronella, coconut, clary sage, clove, coconut, coriander, cumin, cypress, davana, dill, elemi, eucalyptus, fennel, frankincense, galbanum, geranium, ginger, grapefruit, helichrysum, hemp, hyssop, jasmine, juniper, lavandin, lavender, lemon, lemongrass, lime, mandarin, manuka, marjoram, MCT (medium chain triglycerides) oil, melissa, mugwort, mullein, mustard, myrrh, myrtle, neroli, niaouli, nutmeg, oakmoss, orange, oregano, palm, palma rosa, parsley, patchouli, pennyroyal, peppermint, petitgrain, pimento, pine, ravensara, rose, rosemary, rosewood, rue, sage, sandalwood, spearmint, spikenard, tagetes, tangerine, tansy, tarragon, tea tree, thuja, thyme, tuberose, vanilla, vetiver, wintergreen, wormwood, yarrow, ylang, and combinations thereof.

In a further embodiment, the nano spun fiber he nano spun fiber of claim 20, wherein said at least one further oil is added to the acetone solution at a weight percentage of at least 10% of the total weight of the composite.

In a further preferred embodiment, an arthropod repellant material comprising at least one oil and at least one polymer; wherein said at least one oil and at least one polymer are electro spun into a composite and adhering the composite to another material to form the arthropod repellant material.

In a further embodiment, the repellent material wherein the at least one oil is a hemp-based oil.

In a further embodiment, the repellent material wherein the at least one oil is a hemp-based oil comprising at least 10 mg/ml CBD.

In a further embodiment, the repellent material further comprising at last a second oil, selected from the group consisting of: chrysanthemum oil, tea tree oil, lemongrass oil; and combinations thereof.

In a further embodiment, the repellent material comprising at least 10% of the at least one oil.

In a further preferred embodiment, an antibacterial composite material comprising at least 10% of a hemp oil, said hemp oil comprising CBD at a concentration of at least 10 mg/ml and a polymer formed by a process wherein said hemp oil and said polymer are dissolved into a solvent and said solvent is expressed through a spinneret, wherein a voltage is applied at up to 100 kV, wherein the solvent is pressed through the spinneret and forming the antibacterial composite material on a collector.

In a further embodiment, the antibacterial composite wherein the polymer is selected from a biodegradable polymer, a non-biodegradable polymer, or combinations thereof.

In a further embodiment, the antibacterial composite comprising at least a second oil, said at least second oil selected from the group consisting of: allspice, angelica, anise, basil, bay leaf, benzoin, bergamot, birch, bitter almond, black pepper, boldo, buchu, cajuput, calamus, chamomile, camphor, caraway, cardamom, carrot seed, cassia, catnip, cedarwood, chrysanthemum, cinnamon, citronella, coconut, clary sage, clove, coconut, coriander, cumin, cypress, davana, dill, elemi, eucalyptus, fennel, frankincense, galbanum, geranium, ginger, grapefruit, helichrysum, hemp, hyssop, jasmine, juniper, lavandin, lavender, lemon, lemongrass, lime, mandarin, manuka, marjoram, MCT (medium chain triglycerides) oil, melissa, mugwort, mullein, mustard, myrrh, myrtle, neroli, niaouli, nutmeg, oakmoss, orange, oregano, palm, palma rosa, parsley, patchouli, pennyroyal, peppermint, petitgrain, pimento, pine, ravensara, rose, rosemary, rosewood, rue, sage, sandalwood, spearmint, spikenard, tagetes, tangerine, tansy, tarragon, tea tree, thuja, thyme, tuberose, vanilla, vetiver, wintergreen, wormwood, yarrow, ylang, and combinations thereof.

In a further embodiment, the antibacterial composite wherein said polymer is selected from the group consist of: polylactic acid, polyglycolide, polyglycolic acid, polylactide, polyhydroxobutyrate, chitosan, hyaluronic acid, and hydrogels; poly(2-hydroxyethyl-methacrylate), poly(ethylene glycol), chitosan, acetate, rubber, polyethylene, polystyrene, polycarbonate, acrylic resins, polyurethane, polypropylene, polymethylmethacrylate, poly tetrafluoro ethylene, thermoplastic polyurethane, as well as those based on fluorocarbons and certain hydrocarbon polymers are typically non-biodegradable; and combinations thereof.

BRIEF DESCRIPTION OF THE DRAWINGS

FIGS. 4A and 4B depict quantitative results at 24-hour incubation of bacterial loads.

FIGS. 5A and 5B depict quantitative results at 4-hour incubation of bacterial loads.

FIG. 7 depicts an experimental approach.

FIG. 8 depicts a further experimental approach.

FIG. 9 depicts an experimental timeline for a 4-hour incubation.

DETAILED DESCRIPTION OF THE EMBODIMENTS

Figure 1:
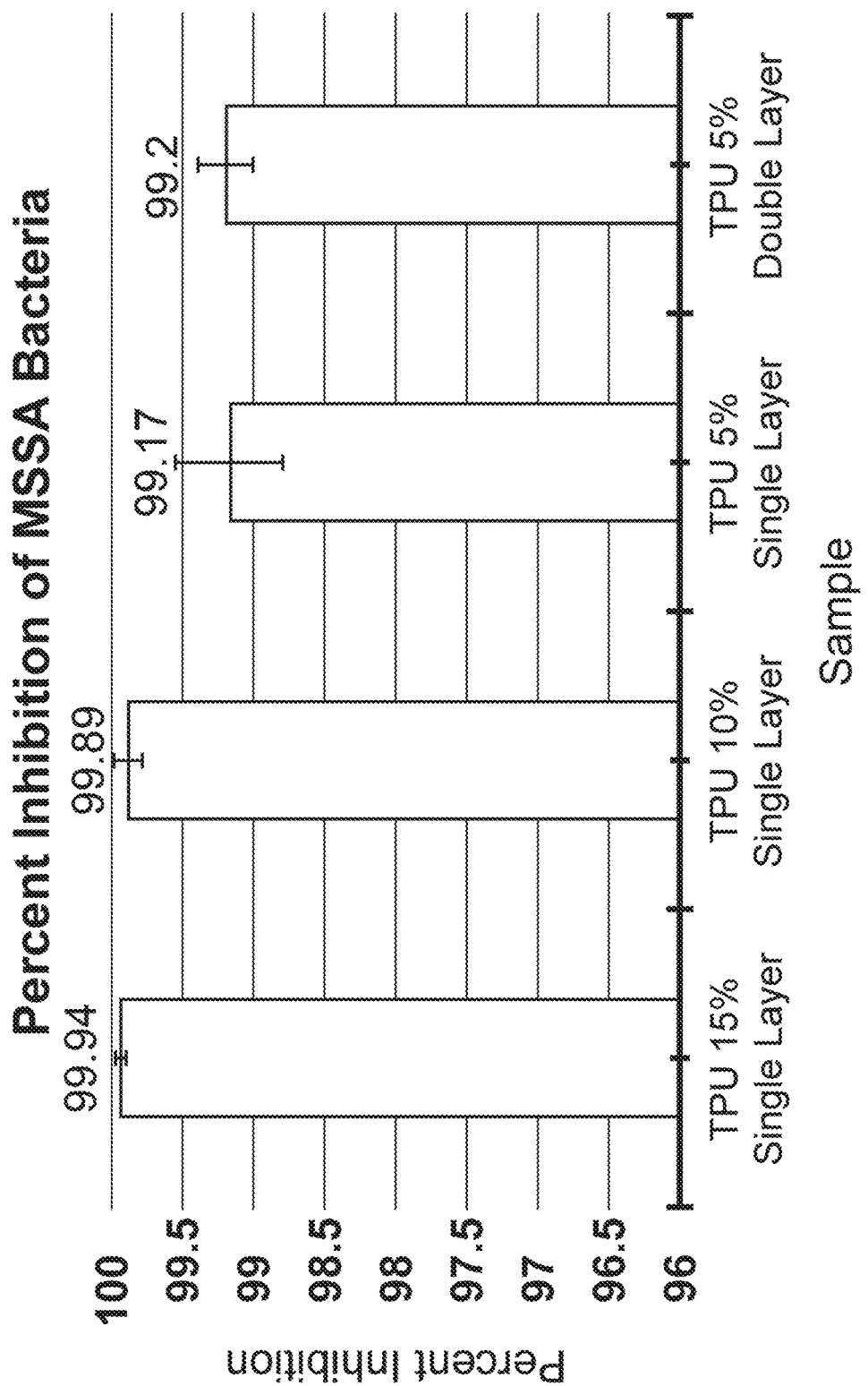
FIG. 1 depicts a graph showing percent inhibition of MSSA bacteria for four different TPU and hemp oil materials.

As an alternative to wood pulp, hemp grows faster and is grown in areas that are not hospitable to trees. Indeed, a primary benefit of hemp plants is their ability to grow rapidly in a wide variety of soils and temperatures. For example, hemp grows in inhospitable areas, is resilient to weed ingrowth, does not require the use of pesticides or herbicides and requires little fertilizer or water to thrive. Hemp can also be utilized to assist in clearing or resting a field, between higher energy/nutrient uptake crops, such as soy and corn. Ultimately, hemp functions as a carbon negative plant, making it highly attractive for use. Of course, a primary value of the hemp plant is the production of seeds and oil containing green material, and the ability to process those seeds for hemp oil and then extractions of green material, including flowers, stems, leaves, and stalks, for oils high in CBD. The term "hemp oil" means any one of oils produced from the cannabis plant, include those pressed from seeds, pressed from other plant materials, or those extracted from the seeds or plant materials.

The processing of oil from seeds is similar to processing oil from olive or grape seed (among others), and is known to those of ordinary skill in the art. Oil can also be pressed from the aerial parts of the plant, for example, the leaf, flower, seed husks, and pressed into an oil. Production of "CBD oil", is through extraction of cannabidiol "CBD" from the aerial parts of the cannabis plant, including the flowers, husks, and leaves, and these processes for extraction are not unique to hemp. Additional terpenes and other components can be added to either of the processed hemp seed oil or from extracted CBD oil, including, for example B-myrcene, B-Caryophyllene, Linalool, a-Pinene, Citral, d-Limonene, and Eucalyptol.

There are numerous known oils that are widely utilized for their aromatic properties and other residential, commercial, and industrial purposes. Other oils include: allspice, angelica, anise, basil, bay leaf, benzoin, bergamot, birch, bitter almond, black pepper, boldo, buchu, cajuput, calamus, chamomile, camphor, caraway, cardamom, carrot seed, cassia, catnip, cedarwood, chrysanthemum, cinnamon, citronella, clary sage, clove, coconut, coriander, cumin, cypress, davana, dill, elemi, eucalyptus, fennel, frankincense, galbanum, geranium, ginger, grapefruit, helichrysum, hemp, hyssop, jasmine, juniper, lavandin, lavender, lemon, lemongrass, lime, mandarin, manuka, marjoram, MCT (medium chain triglycerides) oil, melissa, mugwort, mullein, mustard, myrrh, myrtle, neroli, niaouli, nutmeg, oakmoss, orange, oregano, palm, palma rosa, parsley, patchouli, pennyroyal, peppermint, petitgrain, pimento, pine, ravensara, rose, rosemary, rosewood, rue, sage, sandalwood, spearmint, spikenard, tagetes, tangerine, tansy, tarragon, tea tree, thuja, thyme, tuberose, vanilla, vetiver, wintergreen, wormwood, yarrow, and ylang.

Applicant tested several of these oils, in various concentrations and with different carriers in order to determine efficacy of the material, specifically as imparted into a fiber, or film, and then as a textile material comprising the fiber or film. For example, peppermint oil, eucalyptus oil, tea tree oil, citrus oils, oils from aromatic plants such as lavender and chrysanthemum, and hemp oils were tested under such different conditions in order to determine whether combining oils into a fiber was possible, and the concentrations of the oils suitable for fiber and film formation, as well as the concentration necessary to impart properties from the oils to the fibers.

Key Characteristics of Selected Oils

Hemp oil is a broad term including those oils derived from the cannabis plant. CBD oil refers to an extracted oil from the cannabis plant and contains at least 5% cannabidiol (CBD) per volume of the oil. However, preferred CBD oils comprise more than 5%, and preferably more than 10, more than 15, or more than 20% CBD. The CBD is extracted from green material from the hemp plant, and various strains are utilized to increase the CBD content of the plants. This oil differs from hemp seed oil, which comes from the seeds of the hemp plant. Cold pressed hemp seed oil preserves hemp's nutritious content, so it is often called "Nature's most perfectly balanced oil". Unrefined, cold-pressed hemp seed oil is processed in minimal heat. This means that the oil has not been bleached or deodorized. CBD oil is preferably utilized in the embodiments herein, but hemp seed oil may be included in certain embodiments.

The CBD oil is a full-spectrum oil and refers to when the CBD is extracted from hemp and the extraction contains the same cannabinoids and compounds found in the original hemp plant. Unlike isolated or synthetic cannabinoids, CBD oil contains an array of cannabinoids, as well as many essential vitamins and minerals, fatty acids, protein, chlorophyll, fiber, flavonoids, and terpenes. CBD oil is typically an extract that is then added to a carrier oil, typically either hemp seed oil, MCT oil, or another carrier, and the CBD content is described as mg/ml or as a percentage. Thus a 5% CBD in a 10 ml bottle yields 50 mg of CBD per ml, or a total of 500 ml in the 10 ml bottle. This calculation, per ml is used throughout when CBD is expressed as a percentage. CBD oils also frequently comprise a variety of terpenes, which give the oils their unique flavors, scents, and also imparting certain properties to the oil. These cannabinoids work together in what is called the entourage effect with the additional compounds, such as the terpenes. The entourage effect improves the absorption of active ingredients. Because cannabinoids are chemically polar compounds, sometimes it can be difficult for them to be absorbed. The other natural constituents may help improve their absorbability and viability. Certain hemp oils may incorporate additional cannabinoids or terpenes or flavonoids that allows them to be closer to a full spectrum oil.

Cannabinoids and natural constituents that work together also are able to better overcome bacterial defense mechanisms. While cannabinoids have shown to be potentially effective for treating bacterial infections, bacteria develop defense mechanisms over time. The other non-cannabinoid constituents found in cannabis also have antibacterial properties, utilizing other pathways to combat the bacteria.

Peppermint oil is used as an analgesic, anesthetic, antiseptic, anti-galactagogue, antiphlogistic, antispasmodic, astringent, carminative, cephalic, cholagogue, cordial, decongestant, emmenagogue, expectorant, febrifuge, hepatic, nervine, stimulant, stomachic, sudorific, vasoconstrictor and as a vermifuge.

Health benefits: It is commonly used in the treatment of pain relief, as a way to induce numbness, protect against sepsis, reduce milk flow and discharge, relax spasm, strengthen gums, stop hair loss, and lifts skin. Also, it induces firmness in muscles, stops hemorrhaging, removes gas, is good for brain and memory health, promotes bile discharge, clears congestion and eases breathing. Furthermore, peppermint essential oil relieves obstructed menstruation, expels phlegm & catarrh, reduces fever, is good for liver, and stomach, while promoting perspiration and a slight contraction of the blood vessels.

Lavender essential oil can be calming, sleep-inducing, analgesic, disinfectant, anti-inflammatory, antiseptic, and antifungal.

Health benefits: This oil is beneficial for the treatment of issues with the nervous system, insomnia, pain relief, urine flow, respiratory disorders, skin care, hair care, blood circulation, indigestion, and immune system health.

Eucalyptus oil has a number of important qualities, including anti-inflammatory, antispasmodic, decongestant, deodorant, antiseptic, antibacterial, and stimulating.

Health benefits: It is especially useful in the treatment of respiratory problems, wounds, muscle pain, mental exhaustion, dental care, skin care, diabetes, fever, and intestinal germs.

Tea tree essential oil is antibacterial, antimicrobial, antiviral, fungicide, insecticide, antiseptic, balsamic, cicatrisant, expectorant, stimulant, and sudorific in nature.

Health benefits: This oil is often used to inhibit bacterial, microbial, and viral infections, while also killing insects, protecting wounds from becoming septic, promoting absorption of nutrients, speeding up the healing rate of scars and after marks. Finally, it can cure cough and cold, and stimulate systemic functions and appropriate discharges.

Citrus oils (lemon) Lemon essential oil is an antiseptic, antiviral, astringent, aperitif, bactericidal, disinfectant, febrifuge, hemostatic, restorative, and tonic. Other citrus family oils may be utilized as known to those of ordinary skill in the art, including but not limited to: bergamot, grapefruit, lemon, lime, mandarin, sweet orange, bitter orange, kumquat, among others.

Health benefits: This oil protects from wounds becoming septic, while inhibiting viral and bacterial growth, strengthening gums, and stopping hair loss. Furthermore, it lifts skin, induces firmness in muscles, stops hemorrhage, fights infections, and cures fever.

Chrysanthemum essential oil extracted from the chrysanthemum plant has long been used as an all-natural organic pesticide and insect repellent and contains the chemical pyrethrum. Chrysanthemum oil and extract have also been used in herbal medicine for their antibacterial and antibiotic properties. The oil of the chrysanthemum flower also has a pleasant scent.

When considering certain oils for their antibacterial properties, it is simply meant that antibacterial technology is simply resisting the growth of bacteria. Accordingly, an antibacterial fiber would be a fiber or textile to which an antibacterial agent is added to resist the growth of bacteria. An antimicrobial is an agent that kills microorganisms or inhibits their growth. Antimicrobial fibers then are textiles to which antimicrobial agents have been applied, either at the surface or within the fibers.

To any of the textiles or fibers, it may be advantageous to add certain additional components to impart additional structure or properties to the fiber, or for stabilizing the oil or polymer. Furthermore, additional additives can be introduced to the fiber during spinning or extrusion or combined with dyes or pigments or such additives can be applied as a finishing process.

The embodiments herein describe processes for forming materials comprising of one or more oils with a polymer to spin a fiber. The fibers, advantageously impart characteristics form the oils and the fibers, providing for a new material that is capable of being added to one or more variety of materials wherein the fiber characteristics are imparted to the materials.

Therefore, applicant utilizes the oils together with a polymer to spin a fiber. Electrospinning or nano spinning works by polymer solutions. A solution is generated which comprises the constituent parts, including the polymer and the oil. The polymer solution is then placed into a pipette or a syringe, and then it is pushed to the tip of the pipette, or to a metallic needle (spinneret) by external pumping. Pumping is usually applied by mechanical pistons and generates a flow of the solution in the syringe. Syringes can be oriented both vertically and horizontally with respect to gravity. The spun solution has to exhibit good viscoelastic properties, given by a sufficient amount of entanglements which have to form between macromolecules in the solution. This aspect is one of the most fascinating of electrospinning, since unexpected physical properties can origin in electrified jets of entangled solutions. When a pendant droplet is formed at the spinneret, an electric voltage bias (up to 100 kV, most often of 10-30 kV) is applied between the tip and a collector placed in front of it, at a distance from a few cm to a few tens of cm. The bias is applied by means of a high-voltage generator. The applied voltage is gradually increased, the droplet elongates according forming an apex (Taylor cone and finally electric forces overcome surface tension and a jet is produced. The velocity of the jet can each values of a few m/s, and strain rates are $10^7$ s-1. The solvent quickly evaporates from the jet, and solid nanofibers are finally deposited on the collector.

Key Characteristics of Nanospinning/Electrospinning

High Surface Area to Volume Ratio

The nano-dimension of nanofiber naturally gives it a high surface area to volume ratio. This characteristic makes it incredibly attractive in applications where large surface area is desirable such as in sensors and affinity membranes.

Wide Variety of Polymers and Materials Have Been Used to Form Nanofibers

Electrospinning has been used to make nanofibers from all major classes of materials either directly or indirectly. Although the process is predominantly used to make polymeric nanofibers, ceramic and metal nanofibers have also been constructed indirectly through electro spinning of their precursor material.

Ease of Fiber Functionalization

There are numerous polymers that can be used to electrospin nanofibers. Functionalization of electro spun nanofibers can be achieved through simple blending of polymer solution prior to spinning, post-spinning surface functionalization or using core-shell electro spinning setup. Polymers may include both biodegradable and non-biodegradable polymers.

Biodegradable polymers include those which are durable enough for their particular application, but upon disposal break down under atmospheric conditions. A non-exhaustive list of biodegradable polymers includes polylactic acid, polyglycolide, polyglycolic acid, polylactide, polyhydroxobutyrate, chitosan, hyaluronic acid, and hydrogels. In particular, poly(2-hydroxyethyl-methacrylate), poly(ethylene glycol), chitosan, and hyaluronic acid have been used extensively in the repair of cartilage, ligaments, and tendons.

A non-exhaustive list of non-biodegradable polymers include acetate, rubber, polyethylene, polystyrene, polycarbonate, acrylic resins, polyurethane, polypropylene, and polymethylmethacrylate, thermoplastic polyurethane, as well as those based on fluorocarbons and certain hydrocarbon polymers are typically non-biodegradable. Acetate and thermoplastic polyurethane were primary materials tested in the embodiments herein. Those of skill in the art will recognize other suitable non-biodegradable polymers for inclusion into the embodiments herein.

Combined polymers: In certain instances, it may be suitable to combine polymers, such that the properties of each polymer are imparted into the material. This may include combinations of biodegradable and non-biodegradable polymers.

Ease of Fiber Deposition Onto Other Substrates

Deposition of electro spun fibers requires the collecting surface to have a lower static charge. Electrospun fibers have been routinely deposited on surfaces such as metal, glass, microfibrous mat and water. Accordingly, numerous materials can be used as the collecting surface to allow for easy deposit of the material.

Key Characteristics of Antimicrobial and Antibacterial Fabrics

Antimicrobial fabrics are designed and developed to inhibit or destroy the growth of microorganisms, which include things like bacteria and fungi. Microorganisms can live in a fabric and grow at uncontrolled rates and therefore, antimicrobial fabrics help reduce the spread of disease. That is why antimicrobials are so effective—they prevent or reduce the growth and spread of microorganisms within the fabric. This is especially useful in the healthcare industry where exposure to bacteria and other pathogens is possible on a daily, hourly, basis. This is also useful where mold and fungus can grow easily, such as outdoor fabrics and technical athletic apparel. One can imagine a nearly unlimited set of uses for materials that are capable of resisting growth of bacteria and fungi.

Processes of Producing Fibers Having a Percentage of One or More Oils

Oils were utilized at a percent weight within materials from between 1 and 50% in various tests with one or more polymers. Most preferably, the oil is used in a 1-30% concentration, and even more preferably in a 5-30% concentration. At these ranges, our tests show that the material not only surprisingly maintains efficacy, but that the fiber generated retains characteristics suitable for textile uses but also contain unexpected properties.

Preparation of Oils and Materials for Spinning Fibers and Films

Materials are generated by nano spinning, whether as a single filament, as a plurality of filaments, as several filaments combined together to create fibers, or formed as a film. In each case, a mass of polymer (or mixture of polymers) is measured and added to a container, and a corresponding portion of at least one oil is measured and added to the container to create a suitable percentage of oil as a percent of the total mass. Thus, for the same amount of a polymer, a 10% would contain less oil than a 15%, which would contain less oil than a 20%. The oil is mixed with a polymer and then the combination is preferably dissolved into a solvent carrier. This liquid formation is then expressed under pressure or via gravity through a needle (spinneret), wherein a pendant droplet is formed at the spinneret. A voltage (typically between 1-100 kV) is applied to the needle and a collector is placed in front of the needle. The voltage is gradually increased, and the droplet elongates to form an apex and finally electrical forces overcome surface tension and a jet is produced. The solvent and material are deposited to the collector and the solvent quickly evaporates from the jet leaving the solid fiber on the collector. The fiber contains the raw percentages of the oil and the polymer.

Nanospun CBD Oil:

Nanospun CBD oil was tested between 1 and 50% total weight of the material, with specific tests at 1, 5, 10, 15, 20, 30, and 50% oil concentration, with acetate, with polyester based TPU, and with polyether-based TPU. Other TPU may also include polycaprolactone materials and come in aromatic and aliphatic TPU. Aromatic TPU typically are used where flexibility, strength, and toughness are required, while aliphatic TPU are light and stable and can offer optical clarity. TPU refers to thermoplastic polyurethane, and has two primary classes, polyester based, and polyether based, and within each class, having a variety of molecular weights. TPU is created typically when a polyaddition reaction occurs between a diisocyanate and one or more diols. This polymer is soft and processable when heated, yet hard when cooled and can be reprocessed and repurposed many times without losing structural integrity. A number of varieties of TPU are readily available from any number of vendors in a variety of materials as described herein.

Applicant specifically tested several different TPU materials, each having different physical properties, as expected from their unique structure, but each functioning similarly with regard to the tests herein, with regard to antibacterial properties or with regard to additional properties tested. TPU are often measured by Shore A hardness and density. We used TPU with a Shore A hardness of between 70 A and 100 A—with a density of about 1.19 g/cm$^3$ to 1.22 g/cm$^3$ Accordingly, while initial tests were completed with several different TPU, and also with acetate, remaining tests were performed with a TPU having a Shore A of 95 A and a density of 1.21 g/cm$^3$.

Figure 10:
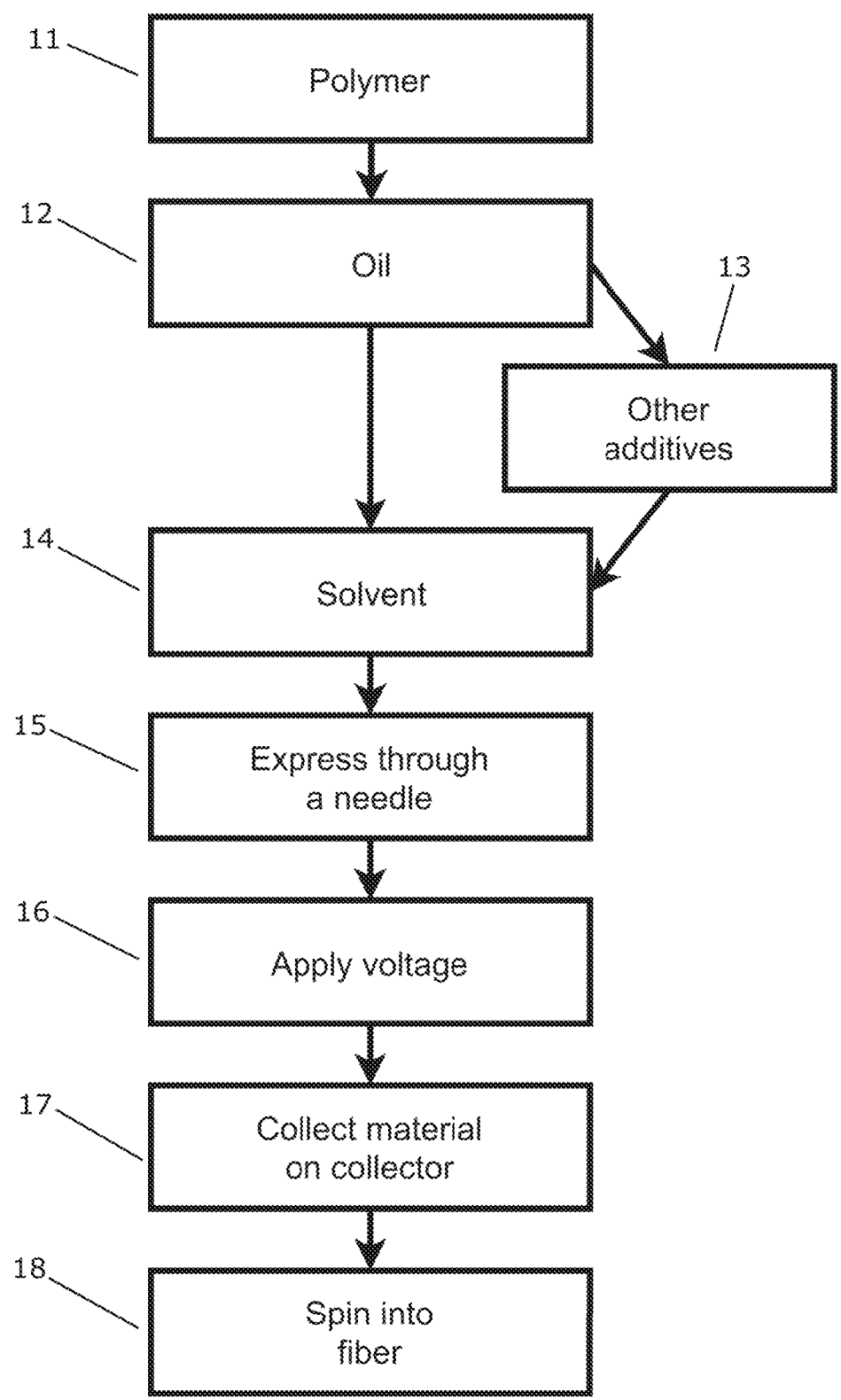
FIG. 10 provides a flowchart of a process for extruding a fiber.

In a first test, 10% of full spectrum CBD oil (20/ml CBD) was added to 90% Acetate and dissolved in a 50%-99% solution of acetone. FIG. 10 details this process with the polymer 11 (acetate) being added to the oil 12, and together added to a solvent 14 of acetone. The material is expressed through a needle 15 and a voltage applied 16, which creates a jet of material, which can be collected on the collector 17, and then spun into a relevant material 18. In certain embodiments, additional additives 13 can be added to the oil and solvent mixture in order to impart additional characteristics to the material. Additional materials using different combinations of oils and polymers were created via this similar general process and tested below Testing Nanospun Hemp Antimicrobial testing was used to test whether the material would react to gram positive or gram-negative bacteria cultures. Different ratios of acetate to CBD oil have been produced on the electro spinner. The ratios include: 100:0 (control), 95:5, 90:10, 85:15 (acetate: CBD oil). Additional studies used higher ratios and combinations of oils with additional details on the ability to kill bacteria or prevent bacterial growth. The antibacterial testing showed that the material killed gram-positive cells, which, for example, would be Staphylococcus bacteria.

Therefore, a preferred method comprises combining a CBD oil with acetate, dissolving the hemp seed oil and acetate into a solution of acetone, and extruding the resulting acetone solution to form a nanospun fiber or film. The percentages of oil within the extruded fiber or film is dependent on the amount of oil included within the acetone solution.

In preferred embodiments, hemp oil is combined with acetate to generate a mixture having 10% or greater CBD oil and the acetate comprising at least 70% of the composition, with each percentage being a percent weight of the total composition. Additional excipients and fillers may be added as necessary, or additional acetate forming the remaining portion of the spun material. Preferably the CBD oil and acetate are dissolved in a nonaqueous solvent, such as acetone. Other suitable solvents (aqueous or nonaqueous) may be utilized that can dissolve the primary acetate material upon particular and stringent conditions.

In a further preferred embodiment, the CBD oil is added to the acetate at between 0.1% to 50%, with preferred ranges between 5 and 25%, and more preferably between 5 and 20%.

Additional antibacterial components may be further added in a percentage between 0.1 and 50% that are effective against gram-negative bacteria.

The above process generated a 10% CBD oil (20 mg/ml CBD) product. We also manufactured materials comprising 0% CBD, 1% CBD, 5% CBD, 15% CBD, 25% CBD, and 50% CBD (each having 20 mg/ml of CBD). The 0% CBD serves as a control for fiber comparison, whereas the 25% and 50% CBD served as test cases for the outer limits of oil percentage that would result in a suitable fiber for manufacturing purposes. While it is possible to make a fiber at 50%, the properties desired in the material were found at lower concentrations of oil, and the fiber at 50% oil concentrations was at the outer limits of the fiber performance.

Our initial tests identified that percentages of at least 5%, 10%, 15%, and 20% CBD oil were most advantageous. 1% hemp, when formed into a fiber possessed little antimicrobial properties, only nominally better than control. Furthermore, the 50% CBD oil possessed excellent antimicrobial properties, but lost some of the physical characteristics and stability of the acetate fiber. Accordingly, the range of 5, 10, 15, and 20% CBD oil appears to be superior for performance both in fiber performance and in antibacterial properties of the resultant fiber.

Accordingly, in preferred embodiments, it would be advantageous to use between 5 and 25% CBD oil, and all combinations between, and more preferably between 10 and 20% CBD oil, in order to make a fiber having superior antimicrobial properties as described herein.

MSSA and MRSA Testing of Full Spectrum CBD (Hemp) Oil

Part One.

Textiles were created with varying weight percentages of Ananda Full Spectrum 600 CBD Oil (20 mg/ml CBD). The samples were contained 0 wt %, 5 wt %, 10 wt %, 20 wt %, and 30 wt % oil concentrations. Most samples were single-layer samples, meaning that they were produced from one run of electrospinning. Samples described as "double-layer" describe samples produced after two runs of electro spinning.

The bacteria species used were Methicillin-sensitive *Staphylococcus aureus* (MSSA) and Methicillin-resistant *Staphylococcus aureus* (MRSA), prepared by the following method: Using sterile technique, a single colony of bacteria, either MSSA or MRSA growing on tryptic soy agar (TSA) plate, was added to 3 mL of tryptic soy broth (TSB) in a 13×100 mm borosilicate glass test tube with a vented slip-cap closure. This culture was incubated with shaking (175 rpm) at 37° C. for 18-19 hours, to a final O.D. 600 nm of 1.1-1.3. The 18 h culture was diluted into fresh 3 mL of TSB in a 13×100 mm borosilicate glass tube to a blank-corrected O.D. 600 nm of 0.043-0.045. This culture was combined with equal volumes of tryptic soy broth slurry (TSB with additional 3 g/L agar) and mixed well by vortexing. 200 μl of TSB slurry/bacterial suspension was pipetted into small epi tubes each containing 200 μl and stored in a −80° C. freezer.

(1) To prepare samples, a 2.5 cm diameter bottle cap was used as a template on fabric (nonwoven or knit) and traced with a scalpel to create the suitable sample for testing. Two circular cut-outs needed per sample. One control sample (containing 0% CBD oil) must be prepared for each trial.

(2) Repeat step (1) on aluminum foil if testing electrospun fabrics—two pieces of aluminum foil needed for each sample.

(3) For knitted samples, cut a 3×3-inch square from aluminum foil. One needed for each sample.

(4) Once cut, place samples and aluminum foil in sterile petri plates. Place open plates in fume hood under UV light for 30 minutes such that one side of each cut-out, fabric and aluminum foil, are exposed to the light. After 30 minutes, turn samples and foil over using autoclaved forceps and sterilize them with UV light for 30 minutes.

(5) While samples are sterilized, prepare epi tubes for bacteria dilutions. Pipette 900 μL sterile water into each tube, except for the 10^1 epi tubes used for initial load dilutions; pipette 450 μL in the 10^1 tubes. Below are the tubes needed per experiment. All are prepared in duplicate:
 a. 10^1, 10^2, 10^3, 10^4, 10^5 for initial load
 b. 10^4 10^5 10^6 for control specimen
 c. 10^4 10^5 for each sample (6) Label tryptic soy agar (TSA) plates in duplicate
 a. 10^3, 10^4, 10^5 for initial load
 b. 10^4, 10^5, 10^6 for control specimen
 c. 10^3, 10^4, 10^5 for each sample (7) 15 minutes before the samples are fully sterilized (45 minutes in UV light), remove frozen bacteria slurry from freezer and thaw on ice (or prepare fresh).

(8) Once thawed, vortex the frozen slurry at 1200 rpm for 15-20 seconds. Repeat 5 times.

(9) To prepare "sandwiches" for each sample:
 a. For electro spun fabrics: place each fabric cut out on a piece of foil. Pipette 10 μL of bacteria slurry on the surface of one of the fabric pieces. With forceps, move the fabric+foil containing no bacteria on to the other fabric+foil pair, such that foil-fabric-bacteria-fabric-foil "sandwich" is created.
 b. For knit fabrics: place fabric cut outs in center of aluminum foil squares. Add 15 μL of slurry to 135 μL sterile water in a small epi tube. Vortex for 5 seconds and repeat 3 times. Pipette 100 μL from the epi tube and evenly dispense onto fabric cut out. Place the other cut out onto the bacteria-containing cut out. With the samples stacked in the center of the foil, fold the left and right one-inch regions of the square over the samples such that a 1×3-inch shape is created.

(10) Using a sterile cell spreader, flatten the foil+fabric systems and put the lid on the petri dish. Set aside.

(11) Repeat steps 9 and 10 for each sample and control. Once completed, stack the petri dishes and place in a half-gallon plastic bag with a damp paper towel. Close the bag, place samples in incubator at 37° C. for four hours. Record time at which samples enter the incubator.

(12) Dilute the bacteria slurry by pipetting 50 μL, of slurry into a 10^1 epi tube containing 450 μL sterile water.

(13) Vortex dilution for 3 seconds at 1200 rpm; repeat 3 times. Pipette 100 μL, of dilution and place into the next epi tube containing 900 μL sterile water (10^2 dilution).

(14) Repeat step (13), taking liquid from 10^2 dilution and adding it to the 10^3 dilution tube.

(15) Repeat step (13), taking liquid from 10^3 solution and adding it to 10^4 dilution tube.

(16) Repeat step (13), taking liquid from 10^4 dilution and adding to 10^5 dilution tube.

(17) Repeat steps (12-16) for duplicate initial load dilutions.

(18) To plate initial load, take 100 μL of liquid from the dilution and plate it on a labeled tryptic soy agar plate.

(19) Place initial load plates in 37° C. incubator (agar-side down) and record time.

Part Two.

(1) Fill large sterile tubes with 10 mL sterile water. One for each sample being tested.

(2) Remove samples from incubator after exactly 4 hours.

(3) Place the foil-fabric-fabric-foil sample into sterile tube with 10 mL water (4) Vortex tube at 1200 rpm for 1 minute.

(5) Repeat steps 3 and 4 for all samples.

(6) Take 100 μL of liquid from the sterile tube after vortexing (10^3 dilution) and place into small epi tube with 900 μL sterile water (10^4 dilution).

(7) Repeat step 6, taking liquid from 10^4 dilution and putting it into 10^5 dilution tube.

(8) Repeat steps 6 and 7 for as many dilutions is needed for each sample (10^3, 10^4, 10^5 for hemp samples, 10^4, 10^5, 10^6 for plain TPU control). Each dilution is done twice for replication.

(9) Take 100 μL of liquid from the dilution and plate it on a labeled tryptic soy agar plate.

(10) Repeat for every dilution and duplicate.
(11) Place plates into incubator for 19-21 hours.
(12) After 19-21 hours, image each plate to count the bacteria.

TABLE 1

Average percent inhibition of MSSA growth for single and double layer TPU samples with varying weight percent of CBD oil.

| Sample | Percent inhibition | Std. Dev |
|---|---|---|
| TPU 15% Single Layer | 99.94 | 0.03 |
| TPU 10% Single Layer | 99.89 | 0.09 |
| TPU 5% Single Layer | 99.17 | 0.38 |
| TPU 5% Double Layer | 99.2 | 0.19 |

A graphical representation of this data is further provided in FIG. 1.

An additional test was performed with MRSA. Table 2 depicts inhibition of MRSA by the materials as described above.

TABLE 2

| Sample | Percent Inhibition | Standard Deviation of Mean |
|---|---|---|
| TPU 30% Single Layer | 99.87 | 0.14 |
| TPU 20% Single Layer | 99.83 | 0.24 |
| TPU 10% Single Layer | 99.95 | 0.07 |
| TPU 5% Single Layer | 99.78 | 0.19 |
| TPU 5% Double Layer | 99.7 | 0.27 |

Figure 3:
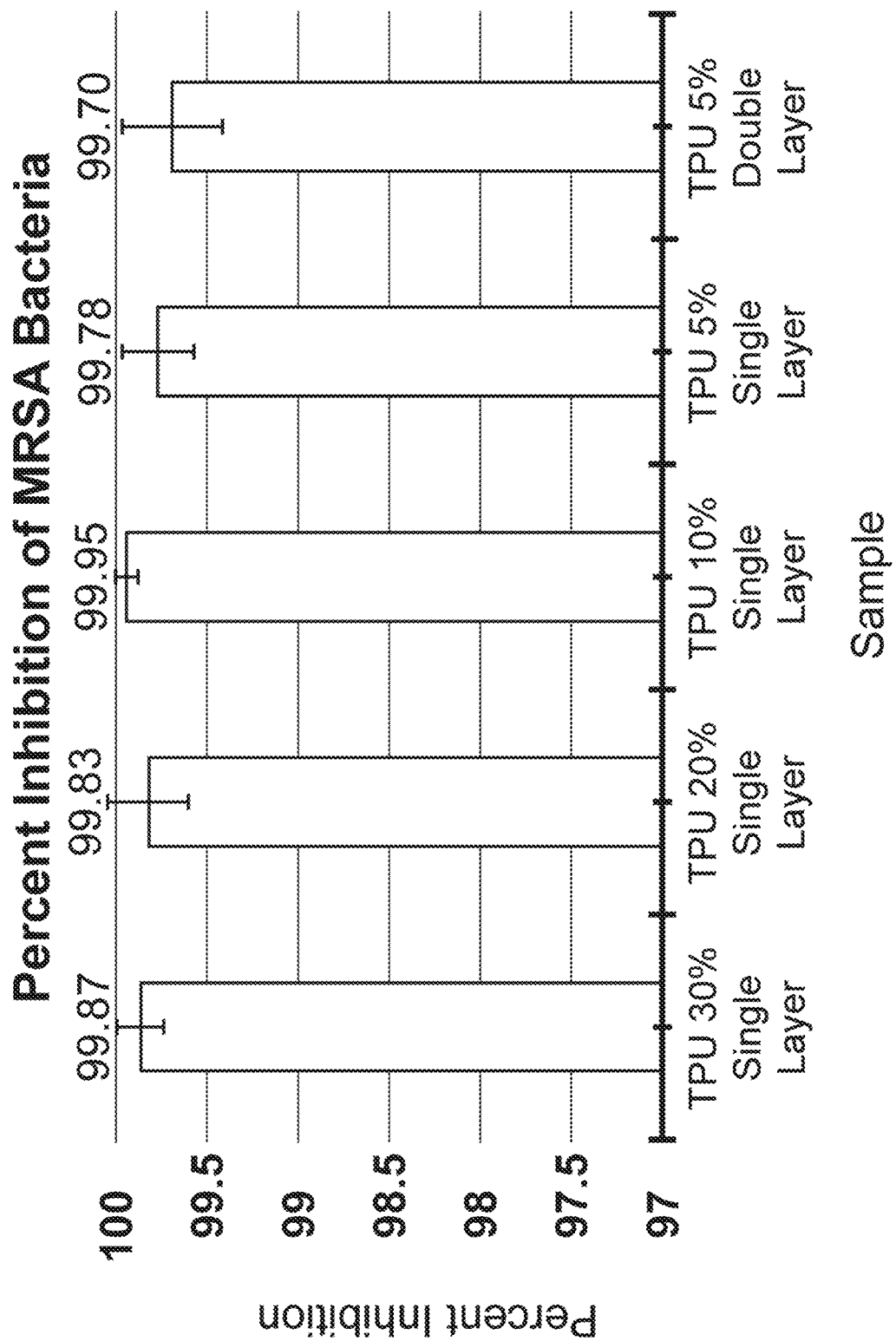
FIG. 3 depicts quantitative results in graphical form of MRSA inhibition.

A graphical representation of this data is further provided in FIG. 3

Control samples are not provided in the data, but visual inspection of the control samples revealed dramatic loads of bacterial colonies. However, the results in the figures show dramatic reductions and inhibition in bacteria colonies.

The first test was actually performed on MSSA with the 15% concentration, to confirm that the material would, at a relatively high concentration of oil, be able to inhibit MSSA growth. Once that was confirmed, lower concentrations were tested to see an appropriate level and concentration for optimal results. Here, even slight changes in inhibition can make a large difference, as bacterial loads grow rapidly under optimal conditions, and thus even the appearance of slight differences, i.e. between 98 and 99% inhibition, has a massive long-term growth. For MSSA, it therefore shows that something having at least 10% oil is optimal, i.e. a single 5% layer and double 5% layer, were significantly inferior for inhibiting growth than the single 10% or single 15% layers. Accordingly, a material, in order to inhibit MSSA is optimized with at least 10% oil.

MRSA is a different bacterium that is often referred to as one of the most difficult to address, once populations are embedded. Again, to test the ability to inhibit growth, a higher concentration CBD material was first tested. A 30% oil material was tested first, and the significant inhibition it generated resulted in additional tests at lower concentrations.

Here, again, the data shows that a concentration of at least 10% yields a substantial improvement as compared to those with 5% oil.

However, with all tests, even materials having 5% CBD oil show significantly improved results, as compared to control.

Figure 2:
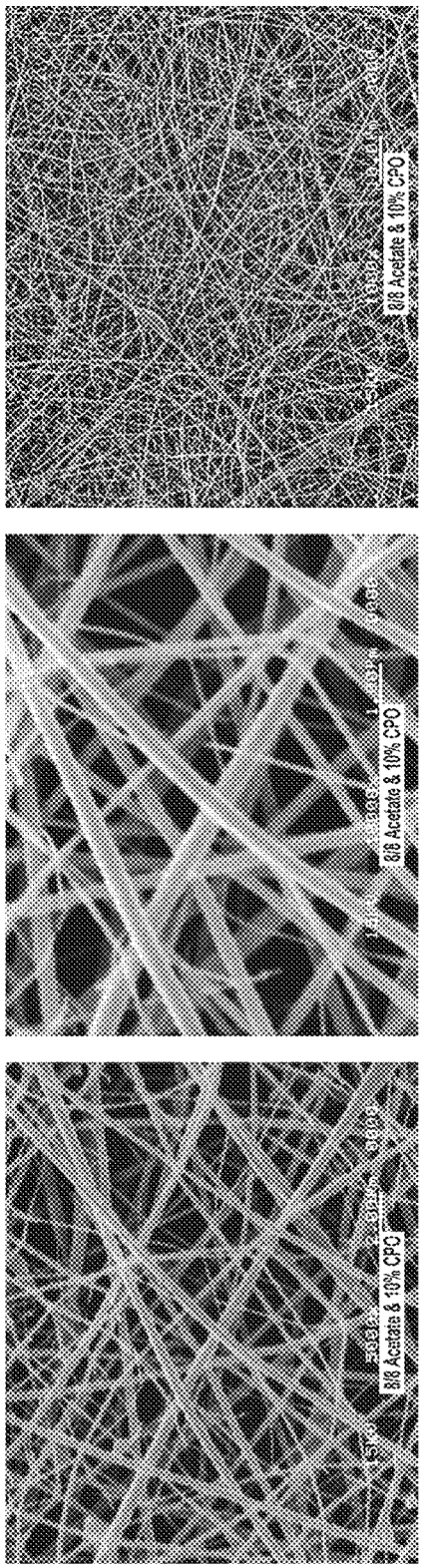
FIG. 2 depicts microscopic images of 90% acetate and 10% CBD oil substrates.

The experimental data utilized a number of different agar plates. These plates are generally not depicted, and instead the data quantified from those studies. For some of the data, a material as described in the present embodiments, using different oils, was created to test the MSSA and MRSA examples as detailed above. FIG. 2, however provides a SEM image at 5000×, 10000×, and 1000× of a material having 90% acetate and 10% hemp seed oil that were electrospun and then tested according to these studies.

Figure 4B:
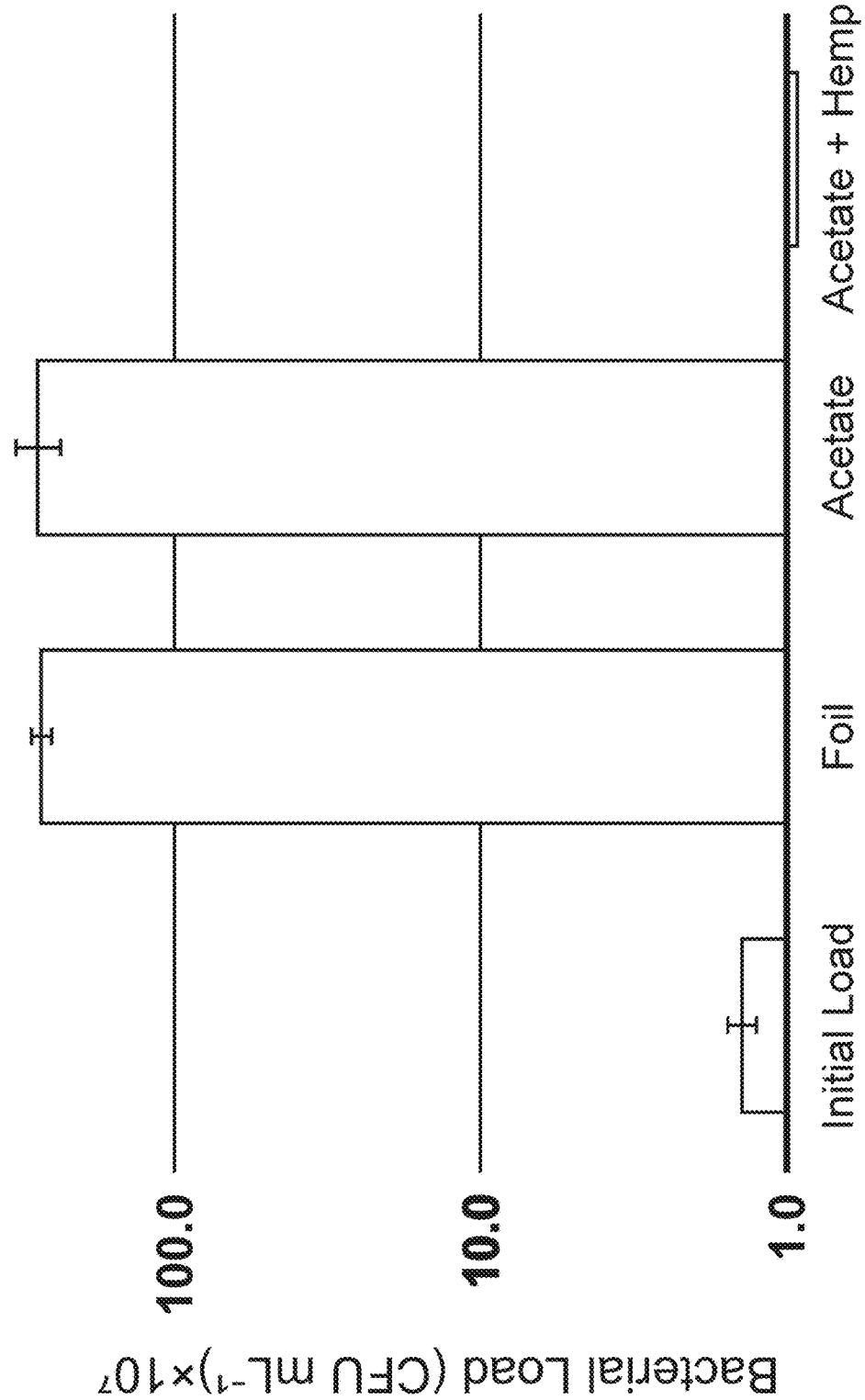

In order to confirm the above results, additional tests were performed using a 10% CBD oil and acetate material. FIGS. 4A and 4B detail results from the growth of S. aureus on TSA (tryptic soy agar) with an application of 10 uL of S. aureus on agar plates. Each plate was incubated for 24 hours at 37° C. and the results imaged and calculated. Visual identification of the samples reveals that the plate with foil, acetate, and hemp oil is nearly bacteria free after the 24-hour incubation period and shows dramatic reductions in bacterial load as compared to the control environments.

Indeed, FIGS. 4A and 4B specifically quantifies this data depicting a reduction in the bacterial load from the initial load, wherein the foil and acetate samples show dramatic bacterial growth and the acetate+CBD showing nearly complete inhibition of growth as compared to the control, which shows dramatic bacterial loads.

This test was repeated in a 4-hour test to confirm these results. Again, 10 uL of S. aureus were incubated on TSA agar plates at 37° C., but just for 4 hours.

Figure 5A:
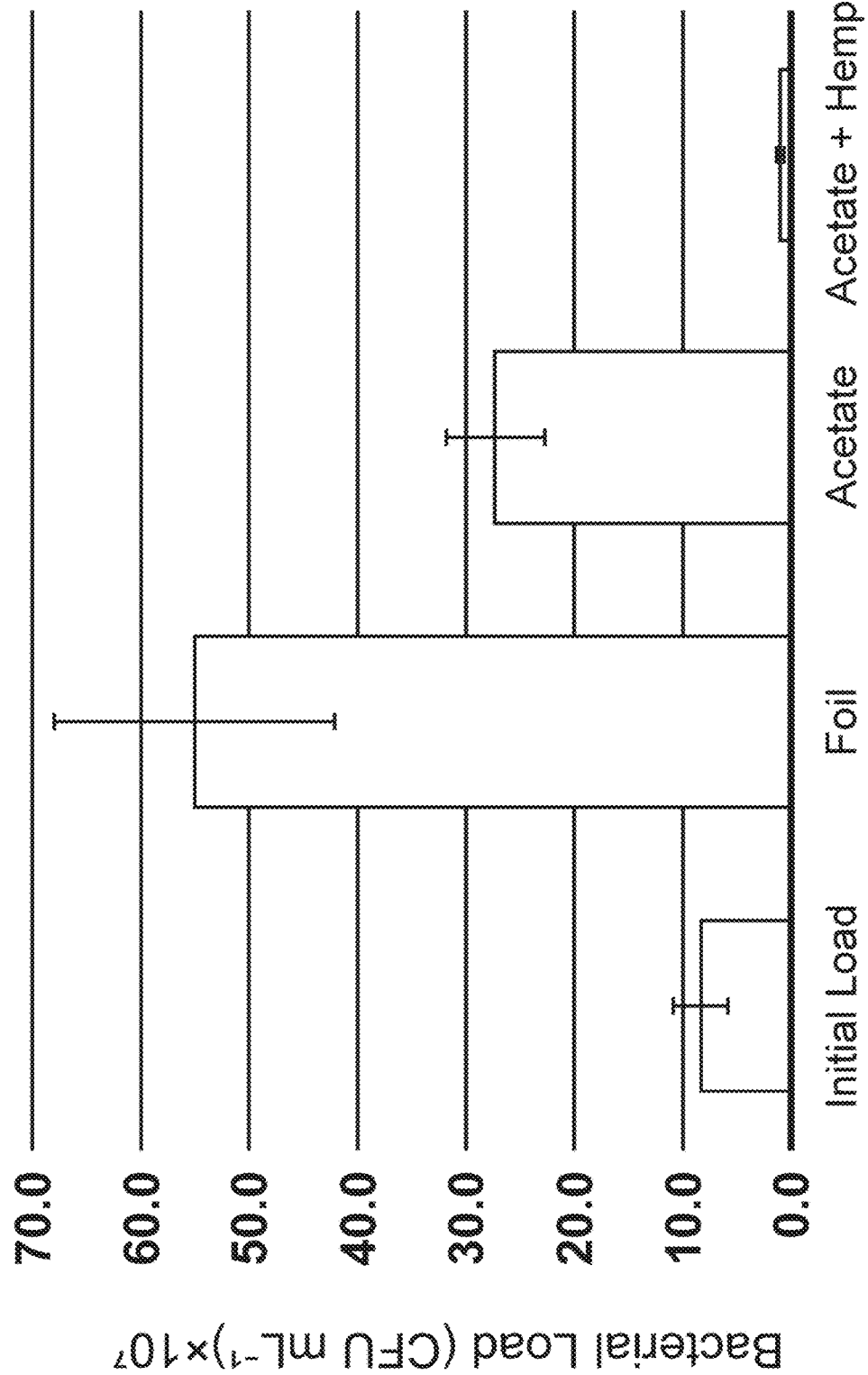

FIGS. 5A and 5B quantify a test regarding 10 uL applications of S. Aureus on 4-hour incubation at 37° C. and shows a dramatic reduction in the bacterial load as compared to the initial load, while the remaining control environments show substantial bacterial growth for the 10% CBD and acetate material.

Figure 6A:
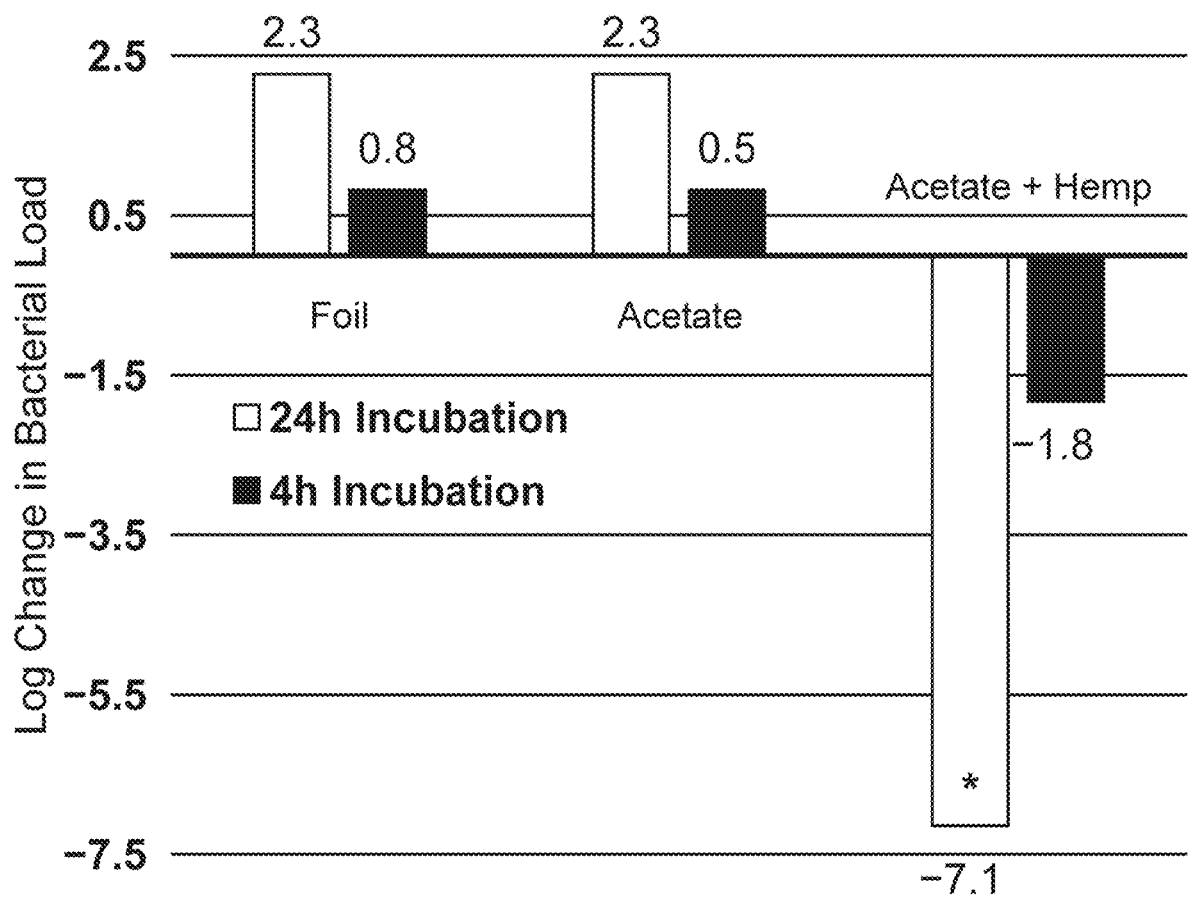
FIGS. 6A and 6B depict a summary of qualitative results of change in bacterial loads.
Figure 6B:
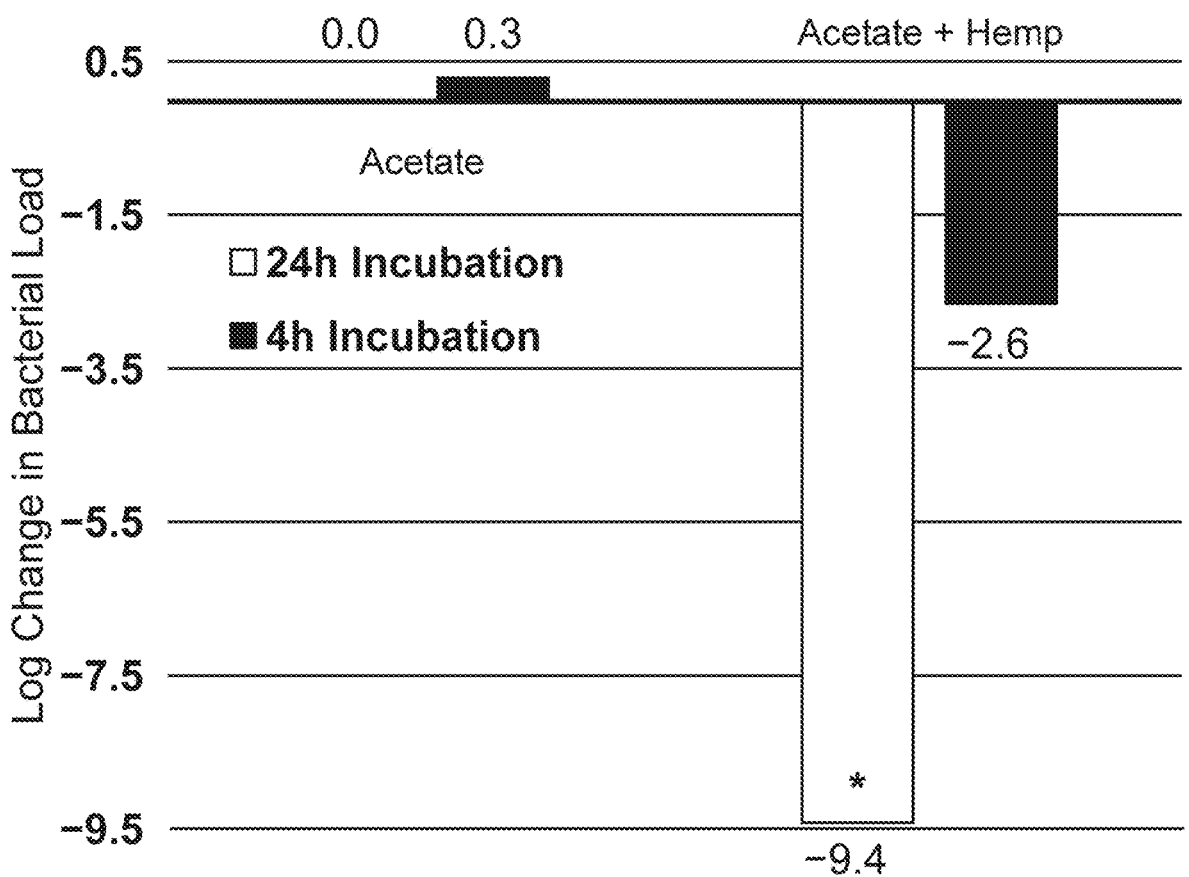

FIGS. 6A and 6B summarize the results and shows a log change in bacterial load with respect to the initial load of the tests from FIGS. 4A-5B. In a 24-hour incubation, the CBD oil samples show a −7.1-log reduction in bacterial load and the 4-hour incubation samples show a −1.8-log reduction. Both the foil and acetate samples increase the bacterial load in the 4- and 24-hour samples. In FIG. 6B then compares the log change with respect only to foil, with dramatic changes in the bacterial load observed in the hemp oil samples. Accordingly, the data confirms that significant differences are found based on application of hemp oil when compared to control samples.

FIG. 7 details the above procedures for testing on foil samples wherein a bacterial culture is generated to test the materials.

FIG. 8 details a more detailed approach when diluting certain samples to generate different concentrations of bacteria loads for testing.

FIG. 9 provides a brief overview of the experimental timeline and processing of samples tested for FIGS. 4A-6B.

In addition to the 10% CBD with acetate materials, several additional oils and polymers were tested to confirm that the process is translatable to other polymers and also with additional oils. These were performed across various concentrations and then tested for antibacterial properties, and in some cases for the ability of a generated material to repel arthropods, including various insects and arachnids, which are taken as representative samples of nuisance arthropods, in which a repellant material is desired.

The following materials were created as provided above, wherein the acetate or TPU was provided with the percentage of oil and then electro spun into a fiber, and the fiber then generated into a material for testing.

5% peppermint oil 95% acetate or 95% TPU
5% eucalyptus oil and 95% acetate or 95% TPU 5% lavender oil and 95% acetate or 95% TPU
5% tea tree oil and 95% acetate or 95% TPU
5% chrysanthemum oil and 95% acetate or 95% TPU
30% peppermint oil and 70% acetate or 70% TPU
30% eucalyptus oil and 70% acetate or 70% TPU
30% lavender oil and 70% acetate or 70% TPU
30% tea tree oil and 70% acetate or 70% TPU
30% chrysanthemum oil and 70% acetate or 70% TPU
10% peppermint oil, 20% CBD oil and 70% acetate or 70% TPU
10% eucalyptus oil, 20% CBD oil and 70% acetate or 70% TPU
10% lavender oil, 20% CBD oil and 70% acetate or 70% TPU
10% tea tree oil, 20% CBD oil and 70% acetate or 70% TPU
10% chrysanthemum oil, 20% CBD oil and 70% acetate or 70% TPU
20% peppermint oil, 10% CBD oil and 70% acetate or 70% TPU
20% eucalyptus oil, 10% CBD oil and 70% acetate or 70% TPU
20% lavender oil, 10% CBD oil and 70% acetate or 70% TPU
20% tea tree oil, 10% CBD oil and 70% acetate or 70% TPU
20% chrysanthemum oil, 10% CBD oil and 70% acetate or 70% TPU
10% lavender oil, 10% tea tree oil, 10% CBD oil, and 70% acetate or 70% TPU.

Each of these combinations was tested for its ability to inhibit MSSA with the results provided in Table 3 below, but each have additional benefits that surprisingly were maintained through the fiber formation process.

TABLE 3

| Oil(s) tested | Percent inhibition of MSSA |
| --- | --- |
| 5% peppermint, no CBD | 84.68% |
| 10% peppermint, 20% CBD | 99.97% |
| 20% peppermint, 10% CBD | 100% |
| 30% peppermint, no CBD | 99.88% |
| 5% eucalyptus, no CBD | 63.79% |
| 10% eucalyptus, 20% CBD | 99.95% |
| 20% eucalyptus, 10% CBD | 99.28% |
| 30% eucalyptus, no CBD | 92.94% |
| 5% tea tree, no CBD | 95.31% |
| 10% tea tree, 20% CBD | 100% |
| 20% tea tree, 10% CBD | 98.49% |
| 30% tea tree, no CBD | 100% |
| 5% chrysanthemum, no CBD | 83.78% |
| 10% chrysanthemum, 20% CBD | 99.94% |
| 20% chrysanthemum, 10% CBD | 100% |
| 30% chrysanthemum, no CBD | 28.68% |

The results of the testing as shown in Table 3, show dramatic improvement with inclusion of a combination of oils for killing MSSA. For example, for nearly each oil, a combination of at least 10% of the CBD oil when admixed with at least 10% of the essential oil results in kill percentages of up to 100%, even repeated over several trials. In preferred embodiments, accordingly, a material comprising at least 10% of each oil was highly effective for killing MSSA. Tea Tree oil also showed dramatic effects with just 30% tea tree oil alone, however, other oils did not show the same efficacy when the essential oil was used without the CBD. Accordingly, it is advantageous to combine oils to increase the rate of kill against bacteria.

Additional Oil Properties

For example, chrysanthemum oil samples (as identified above) were tested for their ability to repel insects. A 24"×24" chamber is created containing an opening for accepting two arms (appendages) and holding insects within the chamber. Female aegyptes mosquitos, n=50 are added to the chamber, and one arm is used as a control, is covered by a cotton material having an acetate backing material with no other oils, and a second arm contains a cotton material having an acetate backing having chrysanthemum oil acetate material or chrysanthemum and CBD acetate material. Total landings on each arm and the duration of landing are calculated over a period of 5 minutes. The control reveals 100 landings with a total dwelling time (time the mosquito remains on the cloth) of 17 minutes. The 30% chrysanthemum oil reveals 25 landings with a total dwelling time of less than 1 minute. Accordingly, there was both a reduction of the landings on the embedded material and a dramatic reduction in the dwelling time, indicating a strong aversion to the chrysanthemum oil acetate material.

This study was tested again with the above combination materials comprising both chrysanthemum and CBD oils with 10% and 20% CBD. The results were maintained, as the 10% CBD and 20% CBD each include less than 20 total landings and dwelling time of less than 1 minute, thus indicating improvements over the material with only chrysanthemum.

This test was repeated with dermacentor variabilis (American dog tick), with appendages touching the base of the container. Again, the total insect population is N=50 and total contact and dwelling time was calculated. Here, the control reveals 57 contacts, and a total dwelling time of 15 minutes, and the 30% chrysanthemum oil reveals a total of 10 contacts and a total dwelling time of less than 1 minute. Here, the dog tick seemed to be repelled from the oil material and actively move away from the chrysanthemum oil material. Indeed, visually, the ticks averted the oil material and, if contacted, quickly removed themselves, while no such occurrence happened with the control.

Again, tests were performed with the combination oils, and similar results were maintained with the 10% and 20% CBD combinations with chrysanthemum, with less than 10 contacts and dwelling time of less than 1 minute.

Finally, an additional insect repellant test was generated using five different materials as indicated below, including lavender oil, CBD, and tea tree oil as a repellant for ants. A small plastic container measuring 14"×11" and a depth of 3.5 inches. The interior walls were coated with olive oil and wiped smooth to prevent the ants from crawling up the sides of the container. Two pieces of fabric measuring 2 inches square are added to the container, one being a control textile and the other an insect repellant fabric.

A test is run for 30 minutes and the total number of contacts with each fabric are counted. A series of three different fabrics are tested, each with 30 ants in the chamber.

TABLE 4

| Ant repellant | | | |
| --- | --- | --- | --- |
| Sample | Control Touches | Sample Touches | Percent Deterrence |
| 5% Lavender | 161 | 124 | 22.98% |
| 20% Lavender, 10% CBD | 150 | 14 | 90.67% |
| 30% Lavender | 174 | 82 | 52.87% |
| 10% Lavender, 10% Tea Tree, 10% CBD | 152 | 17 | 88.82% |

The ant tests again showed dramatic repellant properties for two of the materials, namely ones that included a total of 30% oil. Specifically, those that included both an essential oil and CBD exhibited strong repellant properties. Visually, ants were unlikely to spend long amounts of time on any of the oil samples but would routinely sit on control samples. Ants, if in contact with the oil samples, would investigate and move away, or quickly walk across the material, which was a different behavior than with control samples. Accordingly, while some samples showed lower repellant properties, insect behavior was changed as compared to control.

Therefore, the materials of the present embodiments define a material that possesses strong arthropod repellant properties. The term "repel" or "repellant" means that the arthropods are deterred from the material, as compared to a control material. In a preferred embodiment, a material comprises at least 10% of a first oil, at least 10% of a second oil, and at least one polymer; wherein the polymer and first and second oils are dissolved into a solvent and spun by electrospinning into a fiber; wherein the fiber is sufficient to repel arthropods, including insects and arachnids.

Applications for Nanospun Hemp

Accordingly, the materials defined by the embodiments herein show dramatic reduction in bacterial loads when utilized with CBD oil alone, or in combination with an additional oil. Several oils were tested in combination and those combined oils often showed even greater effects than one oil alone. While oils with at least 5% oil show significant improvements over control, those with 10% oil show further improved performance. Accordingly, preferred embodiments show that a material with at least 10% of a given oil provides for improved results, and so materials are preferably manufactured with a minimum of at least one oil at 10% or more concentration.

This provides for new and exciting materials, to be utilized in existing spaces for improved care where materials, by the nature of the oil within the materials able to reduce bacterial population growth, or in some cases destroy bacterial loads.

Furthermore, in sports and performance materials where technical sports fabrics would have such properties as moisture management, keeping the athlete cool and dry; antimicrobial properties would prevent odor and bacteria growth.

Compression Bandage—bandage compression sleeve that compresses rather than relies on adhesives. This will absorb and retain liquid, be anti-bacterial and durable.

Outdoor Fabrics—awnings, boating fabrics, tents, curtains, and cushions would prevent or reduce mold and bacteria build up.

Bath and kitchen towels—the use of this fiber could prevent the growth and spread of bacteria throughout the kitchen, bathroom and persons using the towel.

In all embodiments, the CBD oil product provides antimicrobial protection. Accordingly, fibers, wherein antimicrobial elements are suitable or desired can advantageously utilize the present invented fiber to prevent formation of, or reduce microbial populations without the need for additional chemicals or materials that may cause rash or discomfort to the skin, or possess other dangers, such as carcinogenic or teratogenic materials, or, ones that are manufactured in a way that is not carbon neutral. Indeed, the fibers generated herein are unique in both their properties and their humble and sustainable origins.

Therefore, preferred embodiments are directed to a process for making an antibacterial material comprising oil and a polymer, wherein said material comprises antibacterial properties sufficient to reduce bacterial formation by 99% or more comprising: mixing CBD oil with said polymer wherein the CBD oil comprises between about 10-30% total weight of the CBD oil and polymer mixture; dissolving the mixture into a solvent; extruding the solvent through an electrospinner into a filament. The filament is collected and forms a film like material, which is advantageously applied to a material.

In preferred embodiments, the process comprises a combination of at least 10% of a first oil, selected from the group consisting of: allspice, angelica, anise, basil, bay leaf, benzoin, bergamot, birch, bitter almond, black pepper, boldo, buchu, cajuput, calamus, chamomile, camphor, caraway, cardamom, carrot seed, cassia, catnip, cedarwood, chrysanthemum, cinnamon, citronella, clary sage, clove, coriander, cumin, cypress, davana, dill, elemi, eucalyptus, fennel, frankincense, galbanum, geranium, ginger, grapefruit, helichrysum, hemp, hyssop, jasmine, juniper, lavandin, lavender, lemon, lemongrass, lime, mandarin, manuka, marjoram, melissa, mugwort, mullein, mustard, myrrh, myrtle, neroli, niaouli, nutmeg, oakmoss, orange, oregano, palma rosa, parsley, patchouli, pennyroyal, peppermint, petitgrain, pimento, pine, ravensara, rose, rosemary, rosewood, rue, sage, sandalwood, spearmint, spikenard, tagetes, tangerine, tansy, tarragon, tea tree, thuja, thyme, tuberose, vanilla, vetiver, wintergreen, wormwood, yarrow, ylang ylang, and combinations thereof, is combined with at least 10% of a second oil, which is a CBD oil (having at least a CBD concentration of 10 mg/ml), and combined with a polymer wherein the total weight of the at least first and at least second oil is at least 20% of the total weight of the combined polymer and oil material; wherein the oil and polymer are dissolved into a solvent and extruded by electrospinning.

In a preferred embodiment, a material having antibacterial properties comprising at least 10% of CBD oil (at least 10mg/ml CBD) and a polymer, wherein the 10% CBD oil and polymer are electro spun to form the material. In a further preferred embodiment, the material comprises at least a second oil, selected from the group consisting of allspice, angelica, anise, basil, bay leaf, benzoin, bergamot, birch, bitter almond, black pepper, boldo, buchu, cajuput, calamus, chamomile, camphor, caraway, cardamom, carrot seed, cassia, catnip, cedarwood, chrysanthemum, cinnamon, citronella, clary sage, clove, coriander, cumin, cypress, davana, dill, elemi, eucalyptus, fennel, frankincense, galbanum, geranium, ginger, grapefruit, helichrysum, hemp, hyssop, jasmine, juniper, lavandin, lavender, lemon, lemongrass, lime, mandarin, manuka, marjoram, melissa, mugwort, mullein, mustard, myrrh, myrtle, neroli, niaouli, nutmeg, oakmoss, orange, oregano, palma rosa, parsley, patchouli, pennyroyal, peppermint, petitgrain, pimento, pine, ravensara, rose, rosemary, rosewood, rue, sage, sandalwood, spearmint, spikenard, tagetes, tangerine, tansy, tarragon, tea tree, thuja, thyme, tuberose, vanilla, vetiver, wintergreen, wormwood, yarrow, ylang ylang, and combinations thereof, wherein the second oil also comprise 10% of the total of the material; forming a material having 10% CBD and 10% of said second oil with a polymer. In a further preferred embodiment, the CBD oil or the second oil, comprising between 10 and 20% of the total of the material. In a further preferred embodiment, the material having 10% of at least 2 or more oils.

In a preferred embodiment, an insect repellant material comprising at least 10% of a CBD oil mixed with a polymer; wherein said 10% CBD oil (at least 10 mg/ml CBD) and said polymer are dissolved into a solvent and electrospun into said insect repellant material. In a preferred embodiment, the insect repellant material comprises at least a second oil selected from the group consisting of: allspice, angelica, anise, basil, bay leaf, benzoin, bergamot, birch, bitter almond, black pepper, boldo, buchu, cajuput, calamus, chamomile, camphor, caraway, cardamom, carrot seed, cassia, catnip, cedarwood, chrysanthemum, cinnamon, citronella, clary sage, clove, coriander, cumin, cypress, davana, dill, elemi, eucalyptus, fennel, frankincense, galbanum, geranium, ginger, grapefruit, helichrysum, hemp, hyssop, jasmine, juniper, lavandin, lavender, lemon, lemongrass, lime, mandarin, manuka, marjoram, melissa, mugwort, mullein, mustard, myrrh, myrtle, neroli, niaouli, nutmeg, oakmoss, orange, oregano, palma rosa, parsley, patchouli, pennyroyal, peppermint, petitgrain, pimento, pine, ravensara, rose, rosemary, rosewood, rue, sage, sandalwood, spearmint, spikenard, tagetes, tangerine, tansy, tarragon, tea tree, thuja, thyme, tuberose, vanilla, vetiver, wintergreen, wormwood, yarrow, ylang ylang, and combinations thereof. In a further embodiment, the insect repellant material comprising at least 10% of two or more oils.

In a preferred embodiment, the insect repellant material comprises oils selected from the group consisting of: CBD, hemp, cedarwood, eucalyptus, lavender, lemon, lemongrass, citronella, peppermint, palma rosa, tea tree, thyme, ylang ylang, and combinations thereof.

What is claimed is:

1. An antibacterial composite material comprising 10%-20% by weight of a cold pressed hemp seed oil comprising cannabidiol at a concentration of at least 10 mg/ml, 10%-20% by weight of a second oil selected from the group consisting of: eucalyptus oil, chrysanthemum oil, lavender oil, tea tree oil, and peppermint oil, and acetate polymer, wherein said composite is formed by a process wherein said hemp oil, said second oil, and said polymer are dissolved into a solvent of acetone and said solvent is expressed through a spinneret, wherein a voltage is applied at up to 100 kV, wherein the solvent is pressed through the spinneret and forming the antibacterial composite material on a collector.

2. The antibacterial composite material of claim 1, further comprising a third component which is effective in reducing the population of gram-negative bacteria when such gram-negative bacteria contact said third component.

3. The antibacterial composite material of claim 1, wherein the cold pressed hemp seed oil comprises at least 20 mg/ml cannabidiol.

4. The antibacterial composite material of claim 1, having arthropod repellent properties.

5. The antibacterial composite material of claim 1, wherein said cold pressed hemp seed oil is included in at least a concentration of 20% by weight of the total weight of the material.

6. The antibacterial composite material of claim 1, wherein the concentration of the cold pressed hemp seed oil and said second oil is 30% by weight.

7. The antibacterial composite material of claim 6, wherein the cold pressed hemp seed oil comprises 10% by weight and the second oil comprises 20% by weight.

8. The antibacterial composite material of claim 6, wherein the cold pressed hemp seed oil comprises 20% by weight and the second oil comprises 10% by weight.

* * * * *